(12) United States Patent
Yayon et al.

(10) Patent No.: US 7,335,508 B2
(45) Date of Patent: Feb. 26, 2008

(54) POROUS PLASMA PROTEIN MATRICES AND METHODS FOR PREPARATION THEREOF

(75) Inventors: Avner Yayon, Moshav Sitria (IL); Hilla Barkay, Rishon L'Zion (IL); Malkit Azachi, Rehovot (IL)

(73) Assignee: ProChon Biotech Ltd., Rehovot (IL)

( * ) Notice: Subject to any disclaimer, the term of this patent is extended or adjusted under 35 U.S.C. 154(b) by 364 days.

(21) Appl. No.: 10/895,961

(22) Filed: Jul. 22, 2004

(65) Prior Publication Data

US 2006/0019389 A1 Jan. 26, 2006

(51) Int. Cl.
  A61F 13/00 (2006.01)
  A61F 2/00 (2006.01)
  C12N 5/06 (2006.01)
  C12N 5/16 (2006.01)

(52) U.S. Cl. .................. 435/343; 424/422; 424/423; 424/428

(58) Field of Classification Search ........... 435/343, 435/343.1, 343.2, 363, 366, 372, 377, 395; 424/422, 423, 428
See application file for complete search history.

(56) References Cited

U.S. PATENT DOCUMENTS

| | | | |
|---|---|---|---|
| 4,442,655 A | 4/1984 | Stroetmann | 53/428 |
| 4,600,574 A | 7/1986 | Lindner et al. | 424/448 |
| 4,642,120 A | 2/1987 | Nevo et al. | 424/442 |
| 4,837,379 A | 6/1989 | Weinberg | 424/548 |
| 5,206,023 A | 4/1993 | Hunziker | 424/423 |
| 5,260,420 A | 11/1993 | Burnouf-Radosevich et al. | 530/382 |
| 5,368,858 A | 11/1994 | Hunziker | 424/423 |
| 5,411,885 A | 5/1995 | Marx | 435/402 |
| 5,443,950 A | 8/1995 | Naughton et al. | 435/1.1 |
| 5,466,462 A | 11/1995 | Rosenthal et al. | 424/426 |
| 5,607,474 A | 3/1997 | Athanasiou et al. | 623/23.71 |
| 5,700,476 A | 12/1997 | Rosenthal et al. | 424/426 |
| 5,842,477 A | 12/1998 | Naughton et al. | 128/898 |
| 5,972,385 A | 10/1999 | Liu et al. | 424/486 |
| 6,274,090 B1 | 8/2001 | Coelho et al. | 422/101 |
| 6,306,424 B1 | 10/2001 | Vyakarnam et al. | 424/426 |
| 6,310,267 B1 | 10/2001 | Rapp | 602/41 |
| 6,333,029 B1 | 12/2001 | Vyakarnam et al. | 424/93.1 |
| 6,398,972 B1 | 6/2002 | Blasetti et al. | 210/782 |
| 6,440,427 B1 | 8/2002 | Wadstrom | 424/400 |
| 6,475,175 B1 | 11/2002 | Rivera et al. | 604/6.02 |
| 6,486,377 B2 | 11/2002 | Rapp | 602/41 |
| 6,534,084 B1 * | 3/2003 | Vyakarnam et al. | 424/443 |
| 6,569,172 B2 | 5/2003 | Asculai et al. | 606/151 |
| 6,599,515 B1 | 7/2003 | Delmotte | 424/422 |

FOREIGN PATENT DOCUMENTS

| | | |
|---|---|---|
| WO | WO 93/16739 | 9/1993 |
| WO | WO 95/25748 | 9/1995 |
| WO | WO 96/24310 | 8/1996 |
| WO | WO 99/56797 | 11/1999 |
| WO | WO 02/095019 | 11/2002 |
| WO | WO 03/007873 * | 1/2003 |
| WO | WO 03/079985 | 10/2003 |
| WO | WO 03/087160 | 10/2003 |
| WO | WO 2004/067704 A2 | 8/2004 |

OTHER PUBLICATIONS

Carr, M.E., "Fibrin formed in plasma is composed of fibers more massive than those formed from purified fibrinogen," *Thromb. Haemost.*, vol. 59, No. 3, pp. 535-539 (1988).

Carr, M.E. et al., "Effect of fibrin structure on plasmin-mediated dissolution of plasma clots," *Blood Coag. Fibrinol.* vol. 6, pp. 567-573 (1995).

Cook, J.L. et al., "Biocompatibility of three-dimensional chondrocyte grafts in large tibial defects of rabbits," *Am J. Vet Res*, vol. 64, pp. 12-20 (2003).

Gao, J. et al., "Repair of osteochondral defect with tissue-engineered two-phase composite material of injectable calcium phosphate and hyaluronan sponge," *Tissue Engin.*, vol. 8, pp. 827-837 (2002).

Gruber, R. et al., "Platelets stimulate proliferation of bone cells: involvement of platelet-derived growth factor, microparticles and membranes," *Clin Oral Implants Res*, vol. 13, pp. 529-535 (2002).

Haisch, A. et al., "Preparation of a pure autologous biodegradable fibrin matrix for tissue engineering," *Med Biol Eng Comput*, vol. 38, pp. 686-689 (2000).

Hunziker, E.B., "Articular cartilage repair: basic science and clinical progress. A review of the current status and prospects," *Osteoarth. Cart.*, vol. 10, pp. 432-463 (2002).

Itokazu, M. et al., The sustained release of antibiotic from freeze-dried fibrin-antibiotic compound and efficacies in a rat model of osteomyelitis, *Infection*, vol. 25, pp. 359-363 (1997).

Sims, C.D. et al., "Tissue engineered neocartilage using plasma derived polymer substrates and chondrocytes," *Plastic & Recon. Surg.*, vol. 101, pp. 1580-1585 (1998).

* cited by examiner

*Primary Examiner*—Blaine Lankford
*Assistant Examiner*—Than Underdahl
(74) *Attorney, Agent, or Firm*—Winston & Strawn LLP

(57) ABSTRACT

The present invention relates to porous freeze-dried plasma protein matrices having an open channel structure and a concentration gradient of plasma proteins crosslinked by the action of thrombin, and methods of producing said matrices. The compositions of the present invention are useful clinically, per se or as cell-bearing implants.

35 Claims, 9 Drawing Sheets

POROUS PLASMA PROTEIN MATRICES AND METHODS FOR PREPARATION THEREOF

FIELD OF THE INVENTION

The present invention relates in general to porous freeze-dried plasma protein biomatrices having open channels useful for clinical applications including as implants for tissue regeneration and tissue engineering. The interconnecting channels, open to the surface, enable cell distribution throughout the biomatrix. The biological and physical characteristics of the matrix are generated by the diffusion of thrombin during formation of the matrix and may be controlled by adjusting the composition and physical properties of the thrombin.

BACKGROUND OF THE INVENTION

Tissue Engineering

Tissue engineering may be defined as the art of reconstructing or regenerating mammalian tissues, both structurally and functionally (Hunziker, Osteoarth. Cart. 10:432-63, 2002). Tissue engineering generally includes the delivery of a synthetic or natural scaffold that serves as an architectural support onto which cells may attach, proliferate, and synthesize new tissue to repair a wound or defect.

An example of a tissue that is prone to damage by disease and trauma is the articular cartilage, one of several types of cartilage in the body, found at the articular surfaces of bones. Damage to cartilage may result from an inflammatory disease such as rheumatoid arthritis, from a degenerative process such as osteoarthritis or from trauma such as intraarticular fracture or following ligament injuries. Cartilage lesions are often associated with pain and reduced function and generally do not heal. Without medical intervention, a patient may require total joint replacement.

Current therapeutic strategies for repairing damaged cartilage encompass procedures that induce a spontaneous repair response and those which reconstruct the tissue in a structural and functional manner. The former includes surgical techniques that expose the subchondral bone thereby allowing the infiltration of bone marrow progenitor cells to initiate the healing response. Often the induced tissue is of a mixed fibrocartilage type, is not durable and the clinical improvements are short lived. The latter strategy includes transplantation of chondral or osteochondral cells or tissue from an autologous or an allogeneic source. Autologous Chondrocyte Transplantation (ACT) relies on transplanting into a cartilage lesion autologous chondrocytes, which have been isolated from a patient's cartilage biopsy and expanded in vitro. In fact, this technique requires a complicated procedure involving two surgical sites and shows limited clinical success.

Matrices useful for tissue regeneration and/or as biocompatible implants useful for tissue culture are well known in the art. These matrices may therefore be considered as substrates for cell growth either in vitro or in vivo. Suitable matrices for tissue growth and/or regeneration include both biodegradable and biostable entities. Among the many candidates that may serve as useful matrices claimed to support tissue growth or regeneration are gels, foams, sheets, and porous structures of different forms and shapes.

Typical bioabsorbable materials for use in the fabrication of porous wound dressings or implants include both synthetic polymers and biopolymers such as structural proteins and polysaccharides. The biopolymers may be selected or manipulated to provide greater or lesser degrees of flexibility or susceptibility to degradation.

U.S. Pat. No. 5,607,474 discloses a molded biodegradable two-layer implant for repair of defects having two dissimilar tissue types. Each layer is prepared separately and subsequently joined together.

U.S. Pat. Nos. 6,306,424; 6,333,029 and 6,534,084 disclose a porous biocompatible foam prepared using a modified polymer-solvent phase separation technique that results in foam having a gradient in stiffness, flexibility, bioabsorption and or pore architecture, associated with a transition in composition. The disclosure teaches foams prepared from synthetic polymers such as aliphatic polyesters.

Fibrin

Fibrinogen is a major plasma protein, which participates in the blood coagulation process. Upon blood vessel injury, fibrinogen is converted to insoluble fibrin which serves as the scaffold for a blood clot. Fibrin is known in the art as a tissue adhesive medical device useful for wound healing and tissue repair. Lyophilized plasma-derived protein concentrate (comprising fibrinogen, Factor XIII and fibronectin), in the presence of calcium ions and the serine protease thrombin, forms an injectable biological sealant (fibrin glue). U.S. Pat. No. 5,411,885 discloses a method of embedding and culturing tissue employing fibrin glue.

The fibrin fiber size, density and rate of degradation of thrombin-induced fibrin gels are affected by several different factors. (Carr M E, Thromb. Haemost., 59(3)535-9, 1988; Carr M E and Alving B M, Blood Coag. Fibrinol. 6:567-73, 1995) The factors include fibrinogen source i.e. pure fibrinogen or plasma, fibrinogen, thrombin and factor XIII concentration, ion content, presence of fibronectin, calcium ions and dextran and other factors. In general, fibrin gels having thicker fibrin fibers, which result from low thrombin concentrations, low ionic strength, higher calcium or fibrinogen concentrations undergo fibrinolysis at a faster rate than fibrin gels having thinner fibers. A plasma protein gradient in a fibrin gel or in a porous, plasma protein matrix has not been taught.

U.S. Pat. No. 4,642,120 teaches the use of fibrinogen-containing glue in combination with autologous mesenchymal or chondrocytic cells to promote repair of cartilage and bone defects. U.S. Pat. No. 5,260,420 discloses a method for preparation and use of biological glue comprising plasma proteins for therapeutic use. U.S. Pat. No. 6,440,427 provides an adhesive composition consisting substantially of fibrin forming components and a viscosity-enhancing polysaccharide such as hyaluronic acid.

U.S. Pat. No. 5,972,385 discloses a lyophilized crosslinked collagen-polysaccharide matrix, with optional fibrin, that is administered per se or in combination with therapeutics for tissue repair. U.S. Pat. Nos. 5,206,023 and 5,368,858 disclose a method and composition for inducing cartilage repair comprising dressing the site with a biodegradable matrix formed by mixing matrix forming material with a proliferative agent and a transforming factor.

A fibrinogen-containing freeze-dried fleece-like structure for use as a wound dressing, filling for bone cavities or support material for release of active materials has been disclosed in U.S. Pat. No. 4,442,655. The structure is prepared by premixing fibrinogen and thrombin solutions, pouring into a mold, freezing and lyophilizing.

A freeze-dried fibrin web for wound healing has been disclosed in U.S. Pat. Nos. 6,310,267 and 6,486,377. The preparation of said web necessitates a single- or multi-stage dialysis of the fibrinogen solution. According to that disclosure, the single-stage or multistage dialysis of the fibrinogen solution changes crucially its composition by reducing the concentration of salts and amino acids. The dialysis is carried out in an aqueous solution of a physiologically compatible inorganic salt and an organic complexing agent.

U.S. Pat. No. 6,599,515 discloses a porous structure of fibrin or fibrinogen wherein the structure in its substantially dry form, has a compression strain of less than 8%, and a creep modulus higher than $1.5 \times 10^6$ Pa. The mechanical properties are obtained by polymerization of the fibrin or fibrinogen materials in the presence of an amount of a calcium-inhibiting agent, preferably an anticoagulant. After hydration, the structure has a porosity wherein at least 50% by volume of the total porosity is formed by channels with an open cross section of more than 500 $\mu m^2$.

A storage stable fibrin sponge containing a blood clotting activator for hemostasis, tissue adhesion, wound healing and cell culture support is disclosed in U.S. Pat. No. 6,548,729. According to that disclosure, the restoration of moisture or water content following lyophilization is crucial for obtaining a soft, adaptable, absorbent sponge. The sponge may further be impregnated with additives such as a blood clotting activator, stabilizers, preservatives and other agents.

A freeze-dried fibrin clot for the slow release of an antibiotic is described by Itokazu (Itokazu et al., Infection 25:359-63, 1997).

U.S. Pat. Nos. 5,466,462 and 5,700,476 teach a bioresorbable heteromorphic sponge comprising a biopolymer matrix structure, at least one substructure and at least one pharmacologically active agent. The substructures allow the incorporation of one or more active agents into the final product for phasic release. U.S. Pat. No. 5,443,950 relates to the growth of cells derived from a desired tissue on a pre-established stromal support matrix. U.S. Pat. No. 5,842,477 discloses a method of in vivo cartilage repair by implanting a biocompatible, three-dimensional scaffold in combination with periosteal/perichondrial tissue and stromal cells, with or without bioactive agents. U.S. Pat. No. 6,569,172 discloses an implantable article for cartilage repair comprising a support matrix, and a mixture of chondrocyte cells and adhesive adhered to an edge of said support matrix.

PCT patent application WO 03/079985 teaches a method of preparing a biomimetic scaffold comprising the steps of providing two or more bio-ink solutions and co-depositing said bio-ink solutions to create the scaffold. Fibrinogen, thrombin and collagen are disclosed as examples of structural bio-inks. A scaffold having a patterned three-dimensional spatial and/or concentration gradient of therapeutic or structural elements is cited, yet a matrix having a plasma protein gradient is neither taught nor suggested.

PCT patent application WO 03/007873 by some of the applicants of the present invention discloses a fibrin matrix comprising plasma proteins and at least one anti-fibrinolytic agent, optionally further comprising agents such as polysaccharides, anionic polysaccharides, glycosaminoglycans, or synthetic polymers added in the preparation to improve certain physical, mechanical and biological properties of the matrix. Copending international patent application PCT/IL2004/000088 by some of the applicants of the present invention teaches a porous plasminogen-free plasma protein sponge and a method of preparing the sponge. The sponge may be prepared by sequential transferring of the thrombin solution and plasma protein solution into a mold or solid receptacle followed by freezing the clotted mixture and lyophilizing or alternatively, premixing the plasma protein solution with thrombin solution and casting into a mold or support prior to achieving clotting; the clotted mixture is frozen and lyophilized.

Collagen

Collagen is the most abundant protein in the body and constitutes a major part of the extracellular matrix. Collagen matrices and sponges useful for tissue regeneration are well known in the art. PCT publication WO 96/24310 discloses a multistage collagen based template or implant characterized by a first layer comprising a dense collagen membrane secured to a second layer comprising a porous collagen matrix.

U.S. Pat. No. 4,837,379 discloses a fibrin-collagen tissue equivalent comprising (i) a hydrated collagen lattice contracted by a contractile agent, such as fibroblasts, and (ii) fibrin. According to that patent, the tissue equivalents are prepared either by casting the collagen and fibrin lattice together or by incorporating the fibrin into the collagen lattice after the lattice is formed. Alternatively, a layered tissue equivalent may be formed.

A porous collagen structure impregnated with a slow setting fibrin adhesive at a fibrin adhesive to collagen volume proportion of at least 1 to 4, useful for osteocartilaginous reconstruction, has been disclosed in WO 93/16739. A method of producing a lyophilized tissue adhesive useful for wound healing based on collagen and fibrin is taught in U.S. Pat. No. 4,600,574. The method comprises the steps of (a) impregnating a tissue compatible flat material selected from collagen, gelatin and polysaccharide with a solution comprised of fibrinogen and factor XIII, and (b) lyophilizing said impregnated flat material to obtain a coherent matrix of said tissue-compatible flat material.

There remains an unmet need for a natural, three-dimensional matrix for use in tissue regeneration and repair that integrates a matrix having optimal pore size, pore distribution and interconnected channels for cell maintenance and nutrient diffusion while it provides a structural support.

SUMMARY OF THE INVENTION

The present invention provides a lyophilized biomatrix comprising plasma proteins and thrombin, wherein the plasma proteins crosslinked by the action of thrombin are present in a concentration gradient along at least one axis of the matrix and form porous structures. It is now disclosed that these open channel structures, interchangeably referred to as biomatrices, matrices, sponges and scaffolds, have unexpected advantageous biological and physical properties. These biomatrices are particularly beneficial for supporting well-distributed cell growth and are useful for a variety of biotechnological and medical applications, including guided tissue repair and regeneration.

A biomatrix comprising a gradient of natural materials, such as plasma proteins, generated by a diffusion gradient of a natural enzyme, such as thrombin, was neither taught nor suggested in the art. The inventors of the present invention have produced, for the first time, biocompatible matrices comprising natural plasma proteins having a gradient in composition and excellent scaffold architecture without resorting to the use of synthetic polymers and complex production methods to achieve these features.

According to one aspect the present invention provides a matrix having at least one surface comprising a porous structure with interconnecting channels that are open to one surface of the matrix and at least one opposing surface having a support function comprising a dense structure with few pores. The at least one surface comprising a porous structure with interconnecting channels provides a large surface area for cell seeding and cell invasion. According to another aspect, these structures are generated by directional diffusion of the thrombin through a homogeneous solution of clottable plasma proteins.

In one aspect the present invention provides a porous, freeze-dried plasma protein matrix comprising plasma proteins and thrombin having two opposing surfaces substantially parallel to the horizontal axis of the matrix and at least one additional surface extending along the periphery of the sponge substantially parallel to the vertical axis, wherein the plasma proteins crosslinked by the action of thrombin are present in a gradient having a higher concentration along one of the opposing surfaces and, wherein the average size of the pores in cross section is smaller along the surface of the matrix exposed to the higher concentration of thrombin.

In one embodiment of the present invention the thrombin is provided at a concentration of about 300 IU/ml to about 1,500 IU/ml, preferably at a concentration of about 500 IU/ml to about 1,000 IU/ml. In another embodiment of the present invention the porous, freeze-dried plasma protein matrix comprises plasma proteins and thrombin in a ratio of about 5:1 (v/v) to about 50:1 (v/v), preferably in a ratio of about 8:1 (v/v) to about 30:1 (v/v), more preferably about 15:1.

In one embodiment the fraction of the matrix exposed to a higher thrombin concentration has fewer and smaller pores and channel openings than the fraction of the matrix exposed to a lower thrombin concentration. In one embodiment the average pore size is about 5 µm to about 30 µm in cross section in the fraction of the matrix exposed to higher thrombin concentration, preferably about 10 µm to about 20 µm, and have an average size of about 20 µm to about 100 µm in cross section in the fraction of the matrix exposed to a lower concentration of thrombin. In one embodiment of the present invention the pores are joined by interconnecting channels.

In some embodiments of the present invention the gradient of plasma proteins crosslinked by thrombin is generated by a thrombin solution comprising at least one viscosity-enhancing agent. In some embodiments the viscosity-enhancing agent is selected from a glycosaminoglycan, a protein, a polysaccharide, a disaccharide and a synthetic polymer. According to one embodiment the viscosity-enhancing agent is a glycosaminoglycan selected from crosslinked hyaluronic acid, non-crosslinked hyaluronic acid, chondroitin sulfate, dextran sulfate, dermatan sulfate, a syndecan and keratan sulfate. In one embodiment the matrix is generated with a thrombin solution comprising non-crosslinked hyaluronic acid at a final concentration of about 0.005% (v/v) to about 0.05% (v/v), preferably at a final concentration of about 0.01% (v/v) to about 0.03% (v/v). In one embodiment the viscosity-enhancing agent is glycerol.

According to another embodiment at least one viscosity-enhancing agent is selected from a soluble protein including albumin or an extracellular matrix protein including collagen, elastin, laminin and fibronectin.

According to yet another embodiment of the present invention the thrombin solution may further comprise at least one crosslinking agent. In one embodiment the crosslinking agent is an enzyme belonging to the family of transglutaminases. In one preferred embodiment the transglutaminase is Factor XIII.

In some embodiments of the present invention the matrix comprises plasma proteins, wherein the plasma proteins comprise fibrinogen or fibrin or a mixture thereof and a crosslinking agent including Factor XIII.

The plasma proteins are purified or partially purified and are obtained from total blood, blood fractions, blood derivative, cryoprecipitate, recombinant proteins, plasma and plasma fractions. According to one embodiment the plasma proteins are obtained from a commercially available source, including native or recombinant proteins. The plasma proteins may be selected from xenogeneic, allogeneic and autologous plasma sources. In some embodiments of the present invention the plasma source is autologous plasma. In one embodiment of the present invention the plasma proteins are substantially devoid of organic chelating agents. According to one preferred embodiment the plasma proteins are substantially devoid of plasminogen.

According to various embodiments of the present invention the matrix comprises plasma proteins at a concentration of about 10 mg/ml to about 40 mg/ml, preferably at a concentration of about 18 mg/ml to about 30 mg/ml, more preferably at a concentration of about 22 to about 27 mg/ml.

The plasma proteins may further comprise at least one additive that imparts additional advantageous biological, physical and mechanical characteristics to the matrix. The at least one additive may be selected from the group consisting of calcium salts, glycosaminoglycans, polysaccharides, and synthetic polymers.

According to one embodiment of the present invention the plasma proteins further comprise a glycosaminoglycan selected from crosslinked hyaluronic acid, non-crosslinked hyaluronic acid, heparin and heparin derivatives and heparin mimetics, chondroitin sulfate, dextran sulfate, dermatan sulfate, heparan sulfate and keratan sulfate.

In one embodiment the plasma proteins comprise non-crosslinked hyaluronic acid at a final concentration of about 0.05%(v/v) to about 0.5% (v/v) more preferably about 0.075% (v/v) to about 0.125% (v/v). In another embodiment the plasma proteins comprise crosslinked hyaluronic acid at a final concentration of about 0.001% to about 0.1% and more preferably about 0.05% (v/v) to about 0.09% (v/v). In yet another embodiment the plasma proteins comprise heparin at a final concentration of about 0.01 µg/ml to about 0.1 mg/ml, preferably at about 0.1 µg/ml to about 1 µg/ml.

In one embodiment of the present invention the matrix has less than 10% residual moisture, more preferably less than about 5% residual moisture.

The present invention further encompasses a porous freeze-dried plasma protein matrix further comprising at least one bioactive agent selected from the group consisting of therapeutic proteins, platelets and platelet supernatant, analgesics, anti-microbial or anti-inflammatory agents and enzymes.

According to another embodiment of the present invention the at least one bioactive agent is a therapeutic protein selected from the group consisting of growth factors and their variants. In one embodiment, the growth factor is selected from a fibroblast growth factor (FGF) and variants thereof. The at least one growth factor may be used at a wide range of concentrations, depending on its potency and the intended application.

For certain applications, sustained or phasic release of a bioactive agent may be preferred. In one embodiment, the at least one growth factor is incorporated in the matrix directly, ab initio. In another embodiment, the at least one growth factor is bound to a carrier molecule such as heparin and is incorporated into the matrix ab initio.

According to another embodiment the present invention provides a porous, freeze-dried plasma protein matrix, further comprising hyaluronic acid, heparin and at least one bioactive agent. Preferably, the hyaluronic acid and the heparin or heparin derivative are incorporated into the sponge ab initio. The bioactive agent, such as a growth factor, may be incorporated into the sponge per se or heparin bound.

In one embodiment the porous freeze-dried plasma protein matrix of the present invention may further comprise at least one agent that affects fibrin fiber thickness, wherein said agent is selected from calcium ions, a salt that alters ionic strength, a serine protease activator, a serine protease inhibitor and dextran sulfate.

According to yet another embodiment the porous freeze-dried plasma protein matrix further comprises at least one membranous structure. According to one preferred embodiment the matrix apposes a membranous structure at one or more surfaces. In one embodiment of the present invention the membranous structure comprises a prefabricated porous or woven planar structure, preferably a matrix, sheet or a mat. In alternate embodiments the membranous structure is selected from a natural or synthetic material. According to one preferred embodiment the planar structure is a natural material comprising crosslinked collagen fibrils.

In one embodiment of the present invention the porous freeze-dried plasma protein matrix further comprises cells. In another embodiment the cells are selected from stem cells or progenitor cells. In yet another embodiment the cells are selected from chondrocytes, osteoblasts, hepatocytes, fibroblasts or mesenchymal, endothelial, epithelial, urothelial, endocrine, neuronal, pancreatic, renal and ocular cell types.

In one embodiment the porous freeze-dried plasma protein matrix of the present invention may have any suitable geometric shape, for example, and without limiting the invention, cylindrical, cuboidal and cube. In another embodiment the matrix of the present invention has a suitable geometric shape adapted to fit a lesion, defect or void into which it is introduced. The lesion, defect or void may be present in any body tissue including skeletal tissue such as cartilage and bone, and other body tissues including liver, bladder, neuronal tissue, pancreas, kidney, heart and breast.

Another aspect of the present invention provides a method of preparing the porous, freeze-dried plasma protein matrix comprising plasma proteins and thrombin having two opposing surfaces substantially parallel to the horizontal axis of the matrix and at least one additional surface extending along the periphery of the sponge substantially parallel to the vertical axis, wherein the plasma proteins crosslinked by the action of thrombin are present in a gradient having a higher concentration along one of the opposing surfaces and, wherein the average size of the pores in cross section is smaller along the surface of the matrix exposed to the higher concentration of thrombin comprising the following steps:

(a) introducing a thrombin solution to a solid receptacle or mold;

(b) layering a plasma protein solution over the thrombin solution in the solid receptacle or mold;

(c) incubating under conditions appropriate to achieve clotting;

(d) freezing the clotted mixture; and (e) lyophilizing the clotted mixture, to obtain a porous matrix.

The method of the present invention may optionally further comprise the steps of (f) seeding the porous matrix with cells; and (g) implanting said cell-bearing porous matrix into an individual in need thereof.

In an alternate embodiment, the method of the present invention may optionally further comprise (h) implanting the porous matrix per se into an individual in need thereof.

According to one embodiment of the invention the porous freeze-dried plasma protein matrix is prepared by transferring the thrombin solution into a mold or solid receptacle, adding the plasma protein solution to the mold or solid receptacle while ensuring minimal mixing of the two solutions, allowing the solutions to form a clot; freezing the clotted mixture and lyophilizing the frozen clotted mixture.

In one embodiment of the present invention the thrombin solution comprises thrombin at a concentration of about 300 IU/ml to about 1,500 IU/ml, preferably at a concentration of about 500 IU/ml to about 1,000 IU/ml.

According to various embodiments of the present invention the plasma protein solution comprises clottable plasma proteins at a concentration of about 10 mg/ml to about 40 mg/ml, preferably at a concentration of about 18 mg/ml to about 30 mg/ml, more preferably at about 22 mg/ml to about 27 mg/ml.

According to one embodiment of the present invention the plasma protein solution and thrombin solution are provided at a ratio of about 5:1 (v/v) to about 50:1 (v/v). In a preferred embodiment the ratio of the plasma protein solution to the thrombin solution is about 8:1 (v/v) to about 30:1 (v/v), preferably at about 15:1 (v/v).

It is now disclosed that the properties of the matrix, including pore size and biodegradability may be controlled by varying the properties of the thrombin solution. The properties of the thrombin solution that may be varied include temperature, viscosity, volume, composition and concentration.

In one embodiment the thrombin solution is chilled to a temperature of about 4° C. and is introduced into the solid receptacle or mold. In other embodiment the thrombin solution comprises a viscosity-enhancing agent. In one or more embodiments of the present invention the thrombin solution comprises at least one viscosity-enhancing agent. In one embodiment the at least one viscosity-enhancing agent is selected from a glycosaminoglycan, a protein, a polysaccharide, disaccharide and a synthetic polymer. In one or more embodiments of the present invention, the at least one viscosity-enhancing agent is a soluble or an extracellular matrix protein selected from albumin, collagen, elastin, laminin and fibronectin. In one exemplary embodiment the thrombin solution comprises collagen. The collagen may be soluble or fibrillar or a combination of both. In another embodiment the viscosity-enhancing agent is glycerol. In yet another embodiment the viscosity-enhancing agent is PEG or a PEG derivative.

In some embodiments of the present invention the thrombin solution comprises a glycosaminoglycan selected from crosslinked hyaluronic acid, non-crosslinked hyaluronic acid, chondroitin sulfate, dextran sulfate, dermatan sulfate, a syndecan, and keratan sulfate. In one embodiment the thrombin solution comprises hyaluronic acid at a final concentration of about 0.005 (v/v) to about 0.05% (v/v), preferably about 0.01% (v/v) to about 0.03% (v/v). In some embodiments the thrombin solution may further comprise at least one bioactive agent, including therapeutic proteins.

The plasma protein solution comprises clottable plasma proteins, the major clottable protein being fibrinogen. In some embodiments the plasma protein solution further comprises a transglutaminase, including factor XIII. In other embodiments the transglutaminase is introduced in the thrombin solution and diffuses into the plasma protein solution.

According to various embodiments of the present invention the plasma protein solution comprises clottable plasma proteins at a concentration sufficient to yield a matrix comprising a final concentration of about 10 mg plasma proteins/ml to about 40 mg plasma proteins/ml, preferably about 18 mg plasma proteins/ml to about 30 mg plasma proteins/ml.

The plasma protein solution may further comprise at least one additive selected from the group consisting of calcium phosphate particles, a glycosaminoglycan, a polysaccharide, and a synthetic polymer. According to one embodiment of the present invention the glycosaminoglycan is selected from crosslinked hyaluronic acid, non-crosslinked hyaluronic acid, heparin and heparin derivatives and heparin mimetics, chondroitin sulfate, dextran sulfate, dermatan sulfate, heparan sulfate and keratan sulfate.

In some embodiment the plasma protein solution further comprises at least one bioactive agent selected from the group consisting of therapeutic proteins, platelets and platelet supernatant, analgesics, anti-microbial or anti-inflammatory agents and enzymes.

According to yet another embodiment of the present invention the matrix further comprises at least one membranous structure. The membranous structure may be introduced into a solid receptacle or mold during any step of the matrix preparation. In one embodiment of the present invention the membranous structure comprises a prefabricated porous or woven planar structure, preferably a matrix, sheet or a mat. In one embodiment the membranous structure is selected from a natural or synthetic material including a membrane comprising crosslinked collagen fibrils.

In one embodiment of the present invention the thrombin solution, the plasma protein solution or both solutions may further comprise particulate matter such as calcium salts including calcium phosphate particles, hydroxyapatite particles, bone chips or glass fibers that are able to impart certain advantageous properties to the matrix.

Another aspect of the present invention provides a method for treating diseased or injured tissue, the method comprising implanting to the site of disease or injury a porous, freeze-dried plasma protein matrix comprising plasma proteins and thrombin, having two opposing surfaces substantially parallel to the horizontal axis of the matrix and at least one additional surface extending along the periphery of the sponge substantially parallel to the vertical axis, wherein the plasma proteins crosslinked by the action of the plasma are present in a gradient having a higher concentration along one of the opposing surfaces and, wherein the average size of the pores in cross section is smaller along the surface of the matrix exposed to the higher concentration of thrombin. The present invention provides therapeutic applications for guided tissue repair and regeneration in an individual in need thereof.

The invention further provides the use of a freeze-dried plasma protein matrix of the invention for treating diseased or injured tissue. It is to be understood that the matrix of the present invention is intended for use in humans and in veterinary applications.

The porous freeze-dried plasma protein matrix of the present invention is useful in treating orthopedic defects inter alia articular cartilage lesions arising from trauma such as an accident or sports injury or disease such as osteoarthritis. In one embodiment the porous plasma protein matrix comprises autologous plasma proteins and autologous chondrocytes.

The porous freeze-dried plasma protein matrix of the invention is useful, inter alia, as an unexpectedly advantageous support for cellular growth. In one embodiment the matrix, either per se or cell-bearing, is useful in reconstructive surgery, for example as a matrix for regenerating and or repairing tissue. In one embodiment, the matrix is inoculated or seeded with cells and the cells are allowed to proliferate in vitro prior to in vivo implantation. In another embodiment, the matrix is seeded with cells that have been cultured or harvested and the sponge comprising the cells is implanted in situ. In one embodiment the matrix is implanted to the defect site prior to cell seeding. In one embodiment the matrix is useful for delivering cells for gene therapy.

These and further embodiments will be apparent from the Figures, detailed description, examples and claims that follow.

BRIEF DESCRIPTION OF THE FIGURES

The present invention will be understood and appreciated more fully from the following detailed description taken in conjunction with the figures in which:

FIG. 1A shows the dry matrix while FIG. 1B shows a cell-bearing matrix in medium.

FIG. 4A shows the matrix periphery and FIG. 4B shows the top center of the matrix.

FIGS. 5A, 5B and 5C show the surface of the matrix exposed to a lower thrombin concentration; FIG. 5D shows the surface of the matrix exposed to a higher thrombin concentration. The arrows indicate pores.

FIG. 8A shows the cells within the matrix after an three day incubation, FIG. 8B shows the cells in the matrix following a two week incubation.

DETAILED DESCRIPTION OF THE INVENTION

Figure 1A:
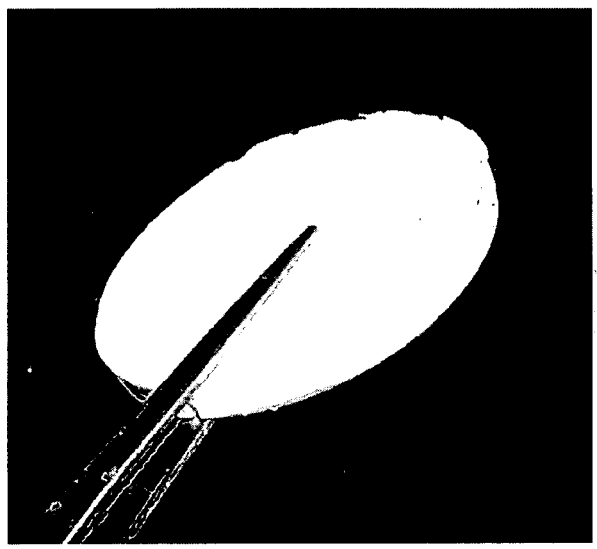
FIGS. 1A and 1B are photographs of a 35 mm diameter matrix.

Though numerous biomatrices comprising plasma or tissue proteins are known in the art to which the present invention pertains, none has proven entirely satisfactory in meeting the criteria required for successful tissue engineering and tissue repair. The present invention provides a lyophilized biomatrix comprising plasma proteins and thrombin, wherein the plasma proteins crosslinked by the action of thrombin are present in a concentration gradient along at least one axis of the matrix, provides a structure having unexpected advantageous physical, mechanical and biological properties. Without wishing to be bound to theory the features of the matrix are generated by a gradient of thrombin through the plasma proteins. Thrombin is acting in a concentration gradient from one surface to the opposing surface. Accordingly, the matrix obtained may have a stepwise gradient or a continuous gradient of plasma proteins that are crosslinked by the action of thrombin. Alternatively, the matrix may comprise separate layers wherein one layer comprises a higher concentration of plasma proteins that are crosslinked by the action of thrombin than another second layer.

The advantageous physical and mechanical properties include:
  dense structural support provided by the action of a high concentration of thrombin along one surface;
  excellent microarchitecture including continuous open pore channels for optimal cell seeding, three dimensional cell distribution and rapid equilibrium of solutes, bioactive materials and waste products; and
  pliability for safe and easy handling and uncomplicated implantation.

The advantageous biological properties of the matrix include:
  biocompatible, non-immunogenic and biodegradable natural products;
  excellent cell attachment and cell distribution throughout the matrix;
  excellent cell proliferation and or differentiation, useful for tissue regeneration and repair;
  may be formulated for controlled release of bioactive agents; and
  plasma proteins may be retrieved from autologous or recombinant material thereby obviating the need for pooled blood sources with the attendant health risks.

In addition, the matrix is prepared using easily accessible materials and according to a simple protocol.

The compositions and methods of the present invention are effective for in vitro and in vivo applications including as cell-bearing implants for tissue engineering and repair.

The matrices of the invention provide all components fundamental for tissue repair, thus facilitating the medical practitioner's task. In addition, the composition of the sponge renders it suitable for minimally invasive surgery of articular cartilage. The sponge may be implanted in a mini-arthrotomy or arthroscopy procedure, thus obviating the need for multiple site surgeries and a full arthrotomy, the standard procedures for ACT.

Definitions

For convenience and clarity certain terms employed in the specification, examples and claims are described herein.

A "biomatrix" as used herein, refers to a porous structure, solid or semi-solid biodegradable substance having pores and interconnecting channels sufficiently large to allow cells to populate, or invade the matrix. The term biomatrix may be used interchangeably with matrix, sponge or scaffold. The plasma protein matrix of the invention wherein the plasma proteins that are crosslinked by the action of thrombin are present in a gradient and that the pores that are present in the fraction of the matrix exposed to a higher thrombin concentration have a smaller diameter and are less abundant than those exposed to a lower thrombin concentration. The matrix-forming components of plasma include fibrinogen and crosslinking agent including Factor XIII, require addition of a cleaving agent, such as thrombin in the presence of bivalent calcium ions, to form a clot. The clot is subsequently freeze-dried yielding a porous plasma protein matrix having interconnecting channels which open to the surface of the matrix.

The plasma protein matrix of the present invention may comprise fibrinogen and or fibrin monomers and or crosslinked fibrin. Fibrinogen is broken down into fibrin monomers by thrombin. Factor XIII, which becomes activated by thrombin in the presence of calcium ions, subsequently forms covalent links between the carboxyl and amino groups of the fibrin monomers to form crosslinked fibrin.

The plasma protein matrix of the present invention is useful as an implant per se, for the culturing of cells or as a cell-bearing tissue replacement implant. Although the examples presented herein refer to the use of the matrix in cartilage and liver repair, it is to be understood that the matrix may be used for tissue reparation and regeneration of many other tissue types including bone, mammary, epithelial, neural, pancreatic and endothelial tissue types.

"Plasma" as used herein refers to the fluid, non-cellular portion of the blood of humans or animals as found prior to coagulation.

"Plasma protein" as used herein refers to the soluble proteins found in the plasma of humans or animals. These include but are not limited to coagulation proteins, albumin, lipoproteins and complement proteins. The major plasma protein is fibrinogen, which upon cleavage, physiologically by thrombin but pathologically by other substances, is converted to fibrin monomers. The fibrin monomers are crosslinked by a transglutaminase, including FactorXIII, to form a stable clot. The term "fibrin matrix" may be used interchangeably with a "plasma protein matrix".

As used herein the term "plasminogen" refers to plasminogen and plasmin. The terms "Substantially devoid of plasminogen" or "plasminogen-free" refer to plasma proteins having less than about 20% plasminogen normally present in plasma, preferably less than about 10% plasminogen normally present in plasma, preferably less than about 5% of the plasminogen normally present in plasma. Plasma normally compromises about 200 mg plasminogen per liter fresh plasma (about 2 µmol/liter).

Factor XIII, is an enzyme of the coagulation cascade which serves to stabilize fibrin by crosslinking the adjacent gamma-chain C-termini of fibrin clots. Although Factor XIII is the preferred crosslinking agent of the present invention, according to certain embodiments the crosslinking agent may be selected from other agents including different types of transglutaminases.

A "substantial absence of organic chelating agents" or "substantially devoid of organic chelating agents" refers to a concentration of less than 1 mm of an organic chelating agent such as EDTA or other organic chelating agents known in the art.

"Platelet rich plasma" or "PRP" as used herein refers to plasma containing platelets. A platelet sample or platelet-derived extract or supernatant may be added exogenously. Alternatively, platelet-rich plasma may serve as the source for plasma proteins. Methods for preparing platelet rich plasma are taught in U.S. Pat. No. 6,475,175 and U.S. Pat. No. 6,398,972.

The term "cell-bearing" as used herein refers to the capacity of the matrix to allow cells to be maintained within its structure. In one embodiment, the cells are able to invade the pores and channels of the matrix and may undergo proliferation and or differentiation.

The term "stem cell" as referred to herein refers to an undifferentiated cell that is capable of proliferation. Stem cells are capable of producing either new stem cells or cells called "progenitor cells" that differentiate to produce the specialized cells found in mammalian tissue and organs.

The term "biocompatible" as used herein refers to materials which have low toxicity, clinically acceptable levels of foreign body reactions in the living body, and affinity with living tissues.

The terms "lyophilize" or "freeze drying" refer to the preparation of a composition in dry form by rapid freezing and dehydration in the frozen state (sometimes referred to as sublimation). This process may take place under vacuum at reduced air pressure resulting in drying at a lower temperature than required at full pressure.

The term "residual moisture" as used herein refers to the amount of moisture remaining in the dried sample. It is referred to as a percent of the weight of the sample. In one embodiment the matrices of the invention have less than 15% residual moisture, preferably less than 10% and more preferably less than 5% residual moisture. The lyophilized matrix may be stored under conditions that preserve its moisture level.

The term "implantation" refers to the insertion of a sponge of the invention into an individual, whereby the implant serves to replace, fully or partially, tissue that has been damaged, diseased or removed.

The "biologically active" or "bioactive agents" incorporated into the sponge, for example, growth factors, platelet and platelet extracts, angiogenic factors, and the like, are advantageous to, in a non-limiting example, encourage a more rapid growth or differentiation of the cells within the implant, or a more rapid vascularization of the implant. Such factors have now been shown to be effectively retained within the sponge and form a source, or depot, of bioactive agent, for sustained release for in vivo or in vitro applications. Other bioactive agents include antibiotics, enzymes, additional plasma proteins or mixtures thereof.

It is to be noted that the pores within the biomatrices of the present invention may be round, elliptical or any random shape. The pore size is easily determined from SEM photographs of the surfaces or cross sections of the matrices. Thus "pore size" or "pore diameter" as referred to herein is determined by measuring the diameter of a pore in cross section in one axis (d1) of a pore and the diameter of the perpendicular axis (d2) of a dried matrix and are presented either as an average of the two measurements or as "d1×d2".

"Polysaccharides" as used herein refer to complex carbohydrates made of more than one saccharide. Included in the definition are anionic polysaccharides, including non-modified as well as chemical derivatives thereof, that contains one negatively charged group (e.g., carboxyl groups at pH values above about 4.0) and includes salts thereof, such as sodium or potassium salts, alkaline earth metal salts such as calcium or magnesium salts. Non-limiting examples of anionic polysaccharides include pectin, alginate, galactans, galactomannans, glucomannans and polyuronic acids.

A "glycosaminoglycan" or "GAG" as used herein refers to a long unbranched polysaccharide molecules found on the cell surface or extracellular matrix. Non-limiting examples of glycosaminoglycan include heparin, chondroitin sulfate, dextran sulfate, dermatan sulfate, heparan sulfate, keratan sulfate, crosslinked or non-crosslinked hyaluronic acid, hexuronyl hexosaminoglycan sulfate, and inositol hexasulfate. Derivatives, salts and mimetics of the above, including low molecular weight heparin are intended to be included in the invention. Without wishing to be bound to theory, the presence of certain GAGs, in particular heparin, aids in immobilizing heparin binding growth factors such as those of the Fibroblast Growth Factor (FGF) family.

The term "cartilage" as used herein, refers to a specialized type of connective tissue that contains chondrocytes embedded in an extracellular matrix. The biochemical composition of cartilage differs according to type but in general comprises collagen, predominantly type II collagen along with other minor types, e.g., types IX and XI, proteoglycans, other proteins and water. Several types of cartilage are recognized in the art, including, for example, hyaline cartilage, articular cartilage, costal cartilage, fibrous cartilage (fibrocartilage), meniscal cartilage, elastic cartilage, auricular cartilage, and yellow cartilage. The production of any type of cartilage is intended to fall within the scope of the invention. The term "chondrocytes" as used herein, refers to cells which are capable of producing components of cartilage tissue.

The term "variant" as used herein refers to a polypeptide sequence that possesses some modified structural property of the wild type or parent protein. For example, the variant may be truncated at either the amino or carboxy terminus- or both termini or may have amino acids deleted, inserted or substituted. It may be antagonistic or agonistic with respect to normal properties of the native protein. The variant may have similar or altered activity as compared to that of the wild type protein.

EMBODIMENTS OF THE INVENTION

In one aspect the present invention provides a porous, freeze-dried plasma protein matrix comprising plasma proteins and thrombin, having two opposing surfaces substantially parallel to the horizontal axis of the matrix and at least one additional surface extending along the periphery of the sponge substantially parallel to the vertical axis; wherein the plasma proteins crosslinked by the action of thrombin are present in a gradient having a higher concentration along one of the opposing surfaces and, wherein the average size of the pores in cross section is smaller along the surface of the matrix exposed to the higher concentration of thrombin.

In one embodiment of the present invention the thrombin is provided in a in a solution having a concentration of about 300 IU/ml to about 1,500 IU/ml, preferably at about 500 to about 1000 IU/ml.

The porous freeze-dried plasma protein matrix comprises plasma proteins and thrombin in a ratio of about 5:1 (v/v) to about 50:1 (v/v), preferably in a ratio of about 8:1 to about 30:1, more preferably 12:1 to about 15:1. Several factors including application and desired rate of degradation may be considered in choosing the preferred plasma protein to thrombin ratio and the plasma protein and thrombin concentrations.

In some embodiments of the present invention the thrombin further comprises a viscosity-enhancing agent that may be selected from at least one glycosaminoglycan, a protein, a polysaccharide, disaccharide and a synthetic polymer. The protein is preferably selected from a soluble protein such as albumin or an extracellular matrix protein including collagen, elastin, laminin and fibronectin. In some embodiments a combination of two or more of the proteins may be incorporated into the matrix. The GAG may be selected from crosslinked hyaluronic acid, non-crosslinked hyaluronic acid, chondroitin sulfate, dextran sulfate, dermatan sulfate, a syndecan and keratan sulfate. In one embodiment the thrombin comprises non-crosslinked hyaluronic acid at a final concentration (v/v) of about 0.005% to about 0.05%, preferably at a final concentration of about 0.01% to about 0.03%. Without wishing to be bound by theory, the presence of a viscosity-enhancing agent may affect the diffusion rate of the thrombin through the plasma proteins.

In one or more embodiments of the present invention the thrombin may comprise at least one therapeutic protein, including growth factors. In one or more embodiment of the present invention the therapeutic protein is a heparin binding protein selected from the family of fibroblast growth factors (FGF), and their variants.

The plasma proteins may further comprise at least one agent that affects fibrin fiber thickness, i.e. an agent including calcium, a salt that alters ionic strength, a serine protease activator, a serine protease inhibitor and dextran sulfate. Without wishing to be bound by theory the thickness of the fibrin fibers may determine the rate of matrix degradation. In general, a thicker fibrin fiber degrades faster than a thinner fibrin fiber. For example, when fibrin is formed from fibrinogen at an ionic strength greater than that of normal plasma a thinner fibrin fiber is formed. In contrast, fibrin fibers formed in the presence of dextran sulfate are thicker than control. (Carr, M E and Alving, B M, Blood Coag. Fibrin., 6:567-573, 1995).

The matrix may be in direct contact with or apposed to a membrane such as a natural polypeptide or synthetic membrane. Incorporation of a membranous layer during preparation of the matrix may increase mechanical strength of the matrix and or may allow for the use of sutures, staples or various fixation devices to hold the matrix in place.

The matrix comprises plasma proteins, the plasma proteins being fibrinogen or fibrin or a combination of both and a crosslinking agent, preferably Factor XIII. The plasma proteins may be obtained from total blood, blood fractions, blood derivative, cryoprecipitate, recombinant proteins, plasma and plasma fractions. According to one embodiment the plasma proteins are obtained from a commercially available source, including native or recombinant proteins. The plasma proteins may be selected from xenogeneic, allogeneic and autologous plasma sources. In certain applications, including cartilage repair, an autologous plasma source is preferred. Some or all of the plasma proteins may be autologous. In one embodiment of the present invention the plasma proteins are substantially devoid of organic chelating agents.

According to one preferred embodiment the plasma proteins are substantially devoid of plasminogen. Freeze-dried plasma protein matrices substantially devoid of plasminogen have been disclosed in copending PCT application PCT/IL2004/000088 of some of the inventors of the present application. Plasminogen may be removed from the plasma by methods known in the art. PCT publication WO 02/095019 discloses a method for specifically removing plasminogen and plasmin in the presence of fibrinogen from a mixture such as blood or cryoprecipitate. PCT publication WO 95/25748 discloses a topical fibrinogen complex essentially free of plasminogen whereby the plasminogen was removed using a Sepharose®-lysine column. Alternatively, some or all of the plasma proteins may be recombinant and consequentially devoid of plasminogen, for example as disclosed in PCT publication WO 99/56797.

The plasma proteins, specifically fibrinogen, is meant to include fibrinogen variants, including the high molecular weight (HMW), the low molecular weight (LMW) and the LMW derivative (LMW') variants, for example as disclosed in WO 03/087160.

The matrix of the invention may further comprise additives that impart other advantageous biological, physical and mechanical characteristics to the matrix. Copending PCT patent application WO 03/007873 of some of the inventors of the present invention discloses a fibrin matrix comprising plasma proteins and at least one anti-fibrinolytic agent, optionally further comprising agents such as polysaccharides, anionic polysaccharides, glycosaminoglycans (GAG), or synthetic polymers to improve certain physical, mechanical and biological properties of the matrix.

According to certain embodiments of the present invention the GAG may be selected from crosslinked hyaluronic acid, non-crosslinked hyaluronic acid, heparin and heparin derivatives and heparin mimetics, chondroitin sulfate, dextran sulfate, dermatan sulfate, heparan sulfate and keratan sulfate. In some embodiments the non-crosslinked hyaluronic acid is present in a final concentration of about 0.05% to about 0.5% (V/V) more preferably about 0.075% to about 0.125%. In another embodiment the crosslinked hyaluronic acid is present in a final concentration of about 0.001% to about 0.1% and more preferably about 0.05% to about 0.09% (V/V).

In certain embodiments, a completely natural plasma protein sponge is desired. Yet, according to another embodiment the present invention may further include the incorporation of additional synthetic and or natural polymers prior to formation of the clot which may modify certain properties of the sponge including physical, mechanical and/or biological properties. These may impart superior characteristics including elasticity, cell attachment, open channels and strength to the sponge. Non-limiting examples of natural polymers include cellulose, pectin, polyuronic acids, hexuronyl hexosaminoglycan sulfate and inositol hexasulfate.

The synthetic polymers useful for the present invention may be non-biodegradable or biodegradable. Examples of non-degradable materials include polytetrafluoroethylene, perfluorinated polymers such as fluorinated ethylene propylene, polypropylene, polyethylene, polyethylene teraphtalate, silicone, silicone rubber, polysufone, polyurethane, non-degradable polycarboxylate, non-degradable polycarbonate, non-degradable polyester, polyacrylic, polyhydroxymethacrylate, polymethylmethacrylate, polyamide such as polyesteramide, and copolymers, block copolymers and blends of the above materials.

Non-limiting examples of degradable materials include hydrolyzable polyesters such as polylactic acid and polyglycolic acid, polyorthoesters, degradable polycarboxylates, degradable polycarbonates, degradable polycaprolactones, polyanhydride, and copolymers, block copolymers and blends of the above materials. Other components include surfactants including lecithin.

In one embodiment, the invention provides a heterogeneous sponge comprising particulate matter such as calcium phosphate crystals or other particles. The particulate matter may be incorporated ab initio in order to provide a matrix having physical or biological characteristics advantageous for certain applications.

Bioactive Agents

In one embodiment the matrix of the invention further comprises at least one bioactive agent, such as a cytokine, a growth factor and their activators, platelets, a bioactive peptide etc. Without wishing to be bound by theory, incorporation of such agents into the sponge of the present invention provides a slow-release or sustained-release mechanism. Sustained release of a bioactive agent may depend on a variety of factors including growth factor concentration, type of glycosaminoglycan incorporated and the concentration of plasma proteins and thrombin.

Without wishing to be bound to theory, as the matrix degrades in vivo, the bioactive agents are released into the surrounding milieu. For example, growth factors, structural proteins or cytokines which enhance the temporal sequence of wound repair, enhance angiogenesis, alter the rate of proliferation or increase the metabolic synthesis of extracellular matrix proteins are useful additives to the matrix of the present invention. The bioactive proteins of the invention are polypeptides or derivatives or variants thereof, obtained from natural, synthetic or recombinant sources, which exhibit the ability to stimulate DNA synthesis and or cell division and or differentiation of a variety of cells, including primary fibroblasts, embryonal stem cells (ESC), adult stem cells, chondrocytes, vascular and corneal endothelial cells, osteoblasts, myoblasts, smooth muscle, neuronal cells and other cell types. Representative proteins include bone growth factors (BMPs, IGF) and fibroblast growth factors and their variants, including FGF2, FGF4, FGF9 and FGF18 for bone and cartilage healing, cartilage growth factor genes (CGF, TGF-β) for cartilage healing, nerve growth factor genes (NGF) and certain FGFs for nerve healing, and general growth factors such as platelet-derived growth factor (PDGF), vascular endothelial growth factor (VEGF), insulin-like growth factor (IGF-1), keratinocyte growth factor (KGF), endothelial derived growth supplement (EDGF), epidermal growth factor (EGF) and other proteins which may enhance the action of the growth factors including heparin sulfate proteoglycans (HSPGs) their mimetics such as dextran sulfate, sucrose octa sulfate or heparin, and fragments thereof. Other factors shown to act on cells forming bone, cartilage or other connective tissue include retinoids, growth hormone (GH), and transferrin. Proteins specific for cartilage repair include cartilage growth factor (CGF), FGFs and TGF-β. Growth factors important for liver regeneration and repair include hepatocyte growth factor, TNFα, interleukin-6, EGF and others. In certain embodiments, the FGF is an FGF having the capacity to induce or enhance liver regeneration, cartilage and bone repair and regeneration and or angiogenesis.

The matrix of the invention, in certain embodiments, may further include one or more of the following biologically active agents: blood platelets, platelet supernatants or extracts and platelet derived proteins; antiseptics, such as methylene blue, and/or one or more drugs including anti-microbials such as antibiotics and antiviral agents; chemotherapeutic agents; anti-rejection agents; analgesics and analgesic combinations; anti-inflammatory agents; enzymes; extracellular matrix protein or adhesion proteins and hormones such as steroids.

Bioactive agents including platelets and platelet supernatant or extract promote the proliferation and differentiation of skeletal cells including chondrocytes and osteoblasts and of other cell types including but not limited to hepatocytes and endothelial cells. Bioactive agents belonging to the class of anti-microbial or anti-inflammatory agents may accelerate the healing process by minimizing infection and inflammation. Enzymes such as chondroitinase or matrix metalloproteinases (MMPs) may be incorporated to aid in the degradation of cartilage, thus stimulating release of cells from the tissue into the matrix and the surrounding milieu.

The growth factors and other bioactive agents may be incorporated at a wide range of concentrations, depending on the application. For certain applications sustained release of a bioactive agent is preferred. Sustained release of a bioactive agent may depend on several factors including growth factor concentration, type of glycosaminoglycan incorporated and plasma protein and thrombin concentration.

According to one non-limiting example the present invention provides a porous freeze-dried plasma protein matrix further comprising at least one glycosaminoglycan and at least one bioactive agent, wherein the at least one glycosaminoglycan is heparin and the at least one bioactive agent is a therapeutic protein belonging to the FGF family of growth factors or a variant thereof. This sponge provides phasic release of the FGF from the matrix and may be beneficial in certain therapeutic applications.

Additionally, cells genetically engineered to express the aforementioned therapeutic proteins or peptides including anti-inflammatory peptides or proteins, growth factors having angiogenic, chemotactic, osteogenic or proliferative effects are included in the present invention. In a non-limiting example, for cartilage repair cells may be transfected with genes selected from a group including transforming growth factor-β (TGF-β), certain FGFs or CGF; for bone repair periosteal or other mesenchymal stem cells or osteoblasts are used per se or are transfected with bone growth factor genes selected from a group including bone morphogenetic protein (BMP) family genes or fibroblast growth factor family genes; for nerve repair neural cells and neural support cells are used per se or are transfected with genes selected from a group including nerve growth factor (NGF) gene or specific FGFs. The matrix is useful inter alia for the delivery of cells in situ to a specific site in the body, such as dopamine expressing cells to Parkinson's patients.

Method of Matrix Preparation

Another aspect of the invention provides a method of preparing the porous, freeze-dried plasma protein matrix comprising plasma proteins and thrombin, having two opposing surfaces substantially parallel to the horizontal axis of the matrix and at least one additional surface extending along the periphery of the sponge substantially parallel to the vertical axis, wherein the plasma proteins crosslinked by the action of thrombin are present in a gradient having a higher concentration along one of the opposing surfaces and, wherein the average size of the pores in cross section is smaller along the surface of the matrix exposed to the higher concentration of thrombin comprising the following steps:

(a) introducing a thrombin solution to a solid receptacle or mold;

(b) layering a plasma protein solution over the thrombin solution in the solid receptacle or mold;

(c) incubating under conditions appropriate to achieve clotting;

(d) freezing the clotted mixture; and (e) lyophilizing the clotted mixture, to obtain a porous matrix.

The method of the present invention may optionally further comprise the steps of (f) seeding the porous matrix with cells; and (g) implanting said cell-bearing porous matrix into an individual in need thereof.

In an alternate embodiment, the method of the present invention may optionally further comprise (h) implanting the porous matrix per se into an individual in need thereof.

According to one embodiment of the invention the porous plasma protein matrix is prepared by transferring the thrombin solution into a mold or solid receptacle, carefully adding the plasma protein solution in order to minimize mixing of the two solutions, allowing the solutions to form a clot; freezing the clotted mixture and lyophilizing.

It is now disclosed that the properties of the matrix, including pore size, pore density, biodegradability may be controlled by adjusting the properties of the thrombin solution. The properties of the thrombin solution that may be varied include temperature, viscosity, volume, composition and concentration.

Without wishing to be bound by theory, a matrix formed using a chilled thrombin solution and or a chilled plasma protein solution undergoes cleavage and a crosslinking at a reduced rate. Alternatively the matrix may be cast using a thrombin solution comprising a viscosity-enhancing agent. Without wishing to be bound by theory, a viscosity-enhancing agent alters the diffusion capacity of the thrombin. Additionally the presence of certain viscosity-enhancing agents such as proteins, polypeptides and glycosaminoglycans may confer additional advantageous properties to the matrix, including improved cell adhesion, enhanced cell proliferation and or differentiation. In one embodiment the thrombin solution comprises at least one viscosity-enhancing agent. The thrombin solution may further comprise a bioactive agent.

In one or more embodiments of the present invention the plasma protein solution comprises fibrinogen and factor XIII. In one embodiment the plasma protein solution consists essentially of fibrinogen; Factor XIII is introduced in the thrombin solution. In one embodiment of the present invention the plasma proteins are obtained from total blood, blood fractions, blood derivative, cryoprecipitate, recombinant proteins, plasma and plasma fractions. According to one embodiment the plasma proteins are obtained from a commercially available source, including native or recombinant proteins. Preferably, the plasma protein solution is substantially devoid of organic chelating agents.

According to various embodiments of the present invention the plasma protein solution is prepared so that the resulting matrix will comprise about 10 mg plasma proteins/ml to about 40 mg plasma proteins/ml, preferably about 18 mg plasma proteins/ml to about 30 mg plasma proteins/ml.

The plasma protein solution may further comprise at least one additive selected from the group consisting of calcium phosphate particles, glycosaminoglycans, polysaccharides, and synthetic polymers.

Preferably the at least one glycosaminoglycan is selected from crosslinked and non-crosslinked hyaluronic acid. According to another embodiment the plasma protein solution comprises hyaluronic acid and calcium phosphate particles.

In one embodiment the plasma protein solution further comprises at least one bioactive agent selected from the group consisting of therapeutic proteins, platelets and platelet supernatant, analgesics, anti-microbial or anti-inflammatory agents and enzymes. The plasma proteins may further comprise one or more antifibrinolytic agents including aprotinin, tranexamic acid, epsilon-aminocaproic acid and alpha-2-macroglobulin.

According to another embodiment of the present invention the at least one bioactive agent is a therapeutic protein selected from the group consisting of growth factors and their variants. In one embodiment, the growth factor is selected from a fibroblast growth factor (FGF) and variants thereof. In one preferred, the FGF is an FGF having the capacity to induce or enhance cartilage, bone or liver repair and regeneration and or angiogenesis. The growth factors may be incorporated at a wide range of concentrations, depending on the potency of the factor and the intended application.

According to one embodiment of the present invention the plasma protein solution comprises hyaluronic acid and or heparin and a therapeutic protein selected from the FGF family of growth factors and variants thereof. Alternatively, the plasma protein solution comprises hyaluronic acid and or heparin and the thrombin solution comprises a therapeutic protein including an FGF. The bioactive agent such as a growth factor may be incorporated into the sponge per se or heparin bound. Heparin may be incorporated into the matrix to a final concentration of about 0.01 ug/ml to about 0.1 mg/mi. Preferably about 0.1 ug/ml to about 1.0 ug/ml. Crosslinked hyaluronic acid maybe incorporated into the matrix to a final concentration of about 0.001% to about 0.1%, more preferably about 0.05% to about 0.09%. Non-crosslinked hyaluronic acid may be incorporated into the matrix to a final concentration of about 0.05% to about 0.5%, more preferably about 0.075% to about 0.125%. In some embodiments both heparin and hyaluronic acid are incorporated into the matrix at respective concentration ranges. Preferably, the additive is incorporated into the matrix ab initio.

Surprisingly, in view of the known function of heparin as an anti-coagulant, the incorporation of heparin into the matrix does not interfere with either the formation of the matrix or the therapeutic benefits of the matrix. Without wishing to be bound by theory, heparin serves primarily to bind FGF or other therapeutic proteins and creates a depot for sustained release of said proteins. In addition, low molecular weight fragments of heparin released from the matrix may function as anti-inflammatory agents and assist in the healing process of diseased or traumatized tissue (U.S. Pat. Nos. 5,474,987; 5,686,431; 5,908,837).

According to yet another embodiment of the present invention the thrombin solution is introduced into a solid receptacle or mold containing a membranous structure. In one preferred embodiment of the present invention the membranous structure lies flat with respect to the solid receptacle or mold. In one embodiment of the present invention the membranous structure comprises a prefabricated porous or woven planar structure, preferably a matrix, sheet or a mat. In one embodiment the membranous structure is selected from a natural or synthetic material. According to one preferred embodiment the planar structure is a natural material comprising crosslinked collagen fibrils.

In one embodiment the method of preparing a plasma protein matrix of the present invention further comprises the steps of shaping the matrix for example by casting in a mold of desired shape, or by cutting or punching the matrix. The matrix may have any suitable geometric shape. In one embodiment the matrix of the present invention has a geometric shape adapted to fit a lesion, defect or void into which it is introduced. The lesion, defect or void may be present in any body tissue including skeletal tissue such as cartilage and bone, and soft tissue such as liver, pancreas, kidney, heart, bladder, breast.

In one embodiment the thrombin solution and or the plasma protein solution further comprise particulate matter such as calcium salts including calcium phosphate particles, hydroxyapatite particles, bone chips or glass fibers that are able to impart advantageous properties to the matrix including strength, additional porosity or phasic release.

The sponge may further comprise at least one bioactive agent, added ab initio to either the thrombin solution or the plasma protein solution.

In its final form prior to use with cells the sponge is substantially dry and contains less than 15% residual moisture, more preferably less than 10% residual moisture.

In another aspect of the present invention provides methods of treating an individual in need thereof. In yet another aspect, the present invention provides use of the fibrin matrix of the invention for treating injured or traumatized tissue, including cartilage and bone defects. The method of treatment described herein is advantageous in that it requires minimal preparation for use by the medical practitioner and provides a less traumatic surgical procedure for the patient.

In one embodiment, the porous fibrin matrix may be used as a coating on synthetic or other implants such as pins and plates, for example, in hip replacement procedures. Thus, the present invention further provides implants or medical devices coated with the comprising the porous fibrin matrix of the invention.

Furthermore, the sponge of the present invention may be used as a component of a two-phase or multi-phase material for tissue repair such as seen in osteochondral defects. In a non-limiting example, one layer may comprise a calcium phosphate material whilst an additional layer may comprise the sponge of the invention.

The plasma proteins may come from a commercial source, natural or recombinant proteins, or may be prepared from plasma. According to one embodiment of the present invention the plasma protein solution derives from allogeneic plasma. According to another embodiment of the present invention, at least one of the components, preferably the plasma proteins, used for preparing the matrix derives from autologous plasma or recombinant proteins. According to another embodiment of the present invention, all of the plasma components used in preparing the matrix are autologous. A stable autologous thrombin component may be isolated from autologous plasma, according to methods known in the art for example those disclosed in U.S. Pat. No. 6,274,090 and Haisch et al (Med Biol Eng Comput 38:686-9, 2000). The plasma proteins may be isolated by a variety of methods, as known in the art and exemplified herein below, resulting in a fibrin matrix having substantially similar properties, as measured by pore size, elasticity, compression and cell bearing capabilities.

In one embodiment, blood is drawn from a patient in need of tissue repair or regeneration, plasma proteins, are isolated from the autologous plasma and a matrix prepared therefrom. The platelets are optionally isolated and returned to the plasma.

According to one embodiment of the present invention a porous plasma protein sponge produced from a plasma protein solution, wherein the fibrinogen solution is subjected to dialysis, preferably with a solution not requiring a complexing agent. While not wishing to be bound by any particular theory the substantial absence of organic complexing agents may provide the matrix of the present invention with properties beneficial to the proliferation and metabolism of certain cell types. As shown in the examples herein, the matrix of the present invention serves as an excellent support for chondrocytes and hepatocytes.

Applications

The porous plasma protein matrix of the invention provides an unexpectedly advantageous support for cellular growth in vitro and in vivo and is useful as a scaffold for tissue engineering and repair applications. The present invention provides all components fundamental for tissue repair, thus facilitating the medical practitioner's task.

The in vivo uses of the plasma matrix are manifold. The matrix may be used as an implant per se, for providing mechanical support to a defective or injured site in situ and/or for providing a matrix within which cells proliferate and differentiate. The cells may be selected from stem cells or progenitor cells or from specialized cells such as chondrocytes, osteoblasts, hepatocytes, or mesenchymal, endothelial, epithelial, urothelial, endocrine, neuronal, pancreatic, renal or ocular cell types.

The matrix of the present invention can be utilized in reconstructive surgery methods for regenerating and/or repairing tissue that have been damaged for example by trauma, surgical procedures or disease. The present invention provides a matrix for use as an implantable scaffold per se for tissue regeneration. According to one embodiment of the invention, the matrix serves as both a physical support and an adhesive substrate for in vivo cell growth. As the cell populations grow and the cells function normally, they begin to secrete their own extracellular matrix (ECM) support. The scaffold polymer is selected to degrade as the need for an artificial support diminishes.

Scaffold applications include the regeneration of tissues such as neuronal, musculoskeletal, cartilaginous, tendonous, hepatic, pancreatic, renal, ocular, arteriovenous, mammary, urinary or any other tissue forming solid or hollow body organs. In orthopedic applications, the matrix may be used per se or in combination with other therapeutic procedures including chondral shaving, laser or abrasion chondroplasty, and drilling or microfracture techniques. Some typical orthopedic applications include joint resurfacing, meniscus repair, non-union fracture repair, craniofacial reconstruction or repair of an invertebral disc.

The matrix of the invention is useful, inter alia, as an unexpectedly advantageous support for in vitro cellular growth. In a certain embodiments of the present invention cells may be cultured on the matrix for subsequent implantation or other laboratory or biomedical applications. Stem cells derived from any tissue or induced to differentiate into a specific tissue type may be utilized. Preferably the cells are derived from autologous tissue. For example, for culturing cartilage, chondrocytes or mesenchymal stem cells may be seeded on the matrix. In specific embodiments of the invention, chondrocytes or chondrocyte progenitor cells can be seeded on the matrix prior to implantation or at the site of implantation. Another in vitro use includes a depot for bioactive agents in cell, tissue or explant culture.

According to certain embodiments, the matrix of the present invention is used as a support for chondrocyte growth and as a scaffold for neo cartilage formation. However, the plasma protein matrix of the invention may be used as a surface useful for tissue culture for any suitable cells, such as mesenchymal cells or other tissue forming cells at different levels of potency. For example, stem cells, mesenchymal stem cells, progenitor cells can be seeded on the matrix of the invention. A lineage-committed progenitor cell is generally considered to be capable of a limited number of mitotic divisions and will eventually differentiate into a specific cell type.

A person skilled in the art can adjust the procedures exemplified below in accordance with specific tissue requirements. Preferably, the matrix of the present invention is implanted per se, and serves as a scaffold for cellular growth in situ. The matrix may be seeded with cells, such as cells that have been expanded in vitro, and implanted. Alternatively, the matrix may be seeded with cells, left to incubate and the sponge comprising the cells implanted at a site in need of tissue repair or regeneration. In certain applications more than one matrix may be implanted at a particular site.

In the reconstruction of structural tissues like cartilage and bone, tissue shape is integral to function, requiring the molding of the matrix into three dimensional configuration articles of varying thickness and shape. Accordingly, the matrix of the invention may be formed to assume a specific shape including a sphere, cube, rod, tube or a sheet. The shape may be determined by the shape of a mold, receptacle or support which may be made of any inert material and may be in contact with the matrix on all sides or on a limited number of sides. The matrix may be shaped in the form of body organs or parts and constitute prostheses. Removing portions of the matrix with scissors, a scalpel, punch, a laser beam or any other cutting or shaping instrument can create any refinements required in the three-dimensional structure.

The methods for seeding cells on the matrix are manifold. In a non-limiting example, the cells may be seeded with the desired cells by any method of seeding including surface seeding, spray seeding or absorption.

Furthermore, the sponge of the present invention may be used as a component of a two-phase or multi-phase material for tissue repair such as seen in osteochondral defects. In a non-limiting example, one layer may comprise a calcium phosphate material whilst an additional layer may comprise the sponge of the invention. Gao et al. (Tissue Engin. 8:827-837, 2002) describe a repair method for osteochondral defects using a composite material comprising an injectable calcium phosphate and a hyaluronic acid sponge.

The following examples are intended to be merely illustrative in nature and to be construed in a non-limitative fashion.

EXAMPLES

Example 1

Preparation of a Plasma Protein Matrix

It is to be understood that many different methods of preparing clottable plasma proteins (CPP=clottable plasma proteins) are known in the art and are useful in the preparation of the matrix of the present invention. The major clottable plasma protein is fibrinogen. A non-limiting example of a protocol for the preparation of a fibrinogen-enriched plasma protein solution is taught in Sims, et al. (Plastic & Recon. Surg. 101:1580-85, 1998). Any source of plasma proteins may be used.

Materials and Methods:

Source of plasma proteins e.g. Quixil (Omrix, Ill.), Beriplast (Aventis, Del.), allogeneic or autologous blood plasma (Stock solution about 40 mg/ml to about 80 mg/ml) or purified fibrinogen (about 67 mg/ml.)

Factor XIII: 60 IU/ml stock solution

Calcium Chloride: about 5 mM

Thrombin: (human, stock solution: 1000 International Units/ml, Omrix, Ill. or 1,500 IU/ml from lyophilized, Aventis Del.)

Hyaluronic acid (HyA); crosslinked (Hylan (Synvisc), approx. MW $6\times10^6$, Genzyme, USA) or non-crosslinked (approx. MW $8\times10^5$, MTF, USA; approx. MW $3.6\times10^6$, BTG, IL.)

Fibronectin (1 mg/ml) was added to the thrombin solution to a final volume of 10%, 25% and 50%. The matrices were prepared as described.

Collagen (Type I, 10 mg/ml) was added to the thrombin solution to a final volume of about 10%, 25% and 50%. The matrices were cast as described below.

Calcium phosphate: Calcium phosphate particles (about 2-4 μm diameter particles) were added to 100 μl thrombin and the matrix cast as described below.

Certain examples of matrix components are shown below in the table 1 below.

| Clottable plasma protein mg/ml | % HyA plasma protein solution | Thrombin Conc (IU/ml) | Ratio plasma proteins: thrombin (v/v) | % HyA in thrombin solution | Clotting temp. (° C.) | Clotting Time (hours) |
|---|---|---|---|---|---|---|
| 20 | 0.075 | 600 | 50:1 | 0 | 17 | 3 |
| 20 | 0.075 | 600 | 30:1 | 0 | 17 | 3 |
| 20 | 0.075 | 600 | 15:1 | 0 | 17 | 3 |
| 24 | 0.1 | 720 | 42:1 | 0 | 17 | 6 |
| 24 | 0.1 | 720 | 30:1 | 0.01 | 17 | 10 |
| 24 | 0.1 | 720 | 30:1 | 0.02 | 17 | 10 |
| 24 | 0.1 | 720 | 30:1 | 0.015 | 17 | 10 |
| 24 | 0.1 | 864 | 30:1 | 0 | 17 | 10 |
| 24 | 0.1 | 864 | 30:1 | 0.01 | 17 | 10 |
| 24 | 0.1 | 864 | 30:1 | 0.01 | 4 | 10 |
| 24 | 0.1 | 864 | 30:1 | 0.03 | 17 | 4, 6, 10 |
| 24 | 0.1 | 864 | 12:1 | 0.02 | 17, 22 | 4, 6 |
| 24 | 0.1 | 720 | 12:1 | 0.01 | 17, 22 | 4, 6 |
| 24 | 0.1 | 720 | 5:1 | 0 | 17 | 3, 6, 10 |
| 25 | 0.1 | 375 | 30:1 | 0.01 | 17 | 10, 24 |
| 25 | 0.1 | 750 | 30:1 | 0.01 | 37 | 2, 3 |
| 25 | 0.1 | 750 | 30:1 | 0.01 | 17 | 6, 10 |
| 25 | 0.1 | 750 | 30:1 | 0 | 17 | 3 |
| 25 | 0.1 | 750 | 10:1 | 0.01 | 37 | 3 |
| 25 | 0.1 | 1500 | 42:1 | 0.01 | 17 | 6, 10 |
| 25 | 0.1 | 1500 | 30:1 | 0.01 | 17 | 10 |
| 27 | 0.1 | 810 | 30:1 | 0.1 | 17 | 10 |

Typically, the "diffusion" sponge was formed in the following manner:

The mold, a solid receptacle or well, was coated with hyaluronic acid (0.01%). The thrombin solution was introduced into the mold. In certain tests the thrombin solution further comprised a viscosity-enhancing material such as collagen, hyaluronic acid, fibronectin, glycerol or other natural or synthetic materials. The plasma protein solution was dispensed over the thrombin solution in the mold; care was taken to prevent mixing of the two solutions. The liquid phases were allowed to incubate at least until a clot formed. Incubation typically continued for several hours, as shown in Table 1. Clots were allowed to form at about 17° C. to about 37° C. The clot was frozen for about 1 hour at about −20° C., −40° C. or at about −70° C. and lyophilized. Exemplary 10 mm matrices were formed by dispensing about 10 ul to about 60 ul thrombin solution and layering with about 300 ul of a plasma protein solution. Exemplary 35 mm matrices were formed by dispensing about 70 ul to about 600 ul thrombin solution and layering with about 3 ml of a plasma protein solution. In certain examples the sponges were seeded with cells including chondrocytes, hepatocytes and other types, see Example 4.

A sponge of any size and shape may be cast. A 35 mm diameter sponge is particularly useful for the treatment of larger lesions, such as those that may develop in osteoarthritis. The matrix may be shaped either before or following cell seeding. In the laboratory, sterile plates having 6, 12, 48 or 96 wells were typically used for casting.

Figure 1B:
Figure 1C:
FIG. 1C shows a cell-bearing sponge following implantation into an irregular shaped defect that was introduced into the articular cartilage of a pig's knee (arrow).

An example of a dry 35 mm diameter sponge is shown in FIG. 1A (3 ml CPP solution: 24 mg/ml CPP, 0.1% HyA; 72 μl thrombin solution: 720 IU/ml, 0.01% HyA). A photograph of a cell-bearing sponge is shown in FIG. 1B and the cell-bearing sponge implanted into a lesion introduced into the articular surface of a pig's knee is shown in FIG. 1C.

Matrices prepared from purified fibrinogen, were cast in the following manner:

A fibrinogen stock solution was prepared by mixing 432 μl purified fibrinogen, 120 μl hyaluronic acid and 650 μl purified distilled water. Matrices comprising different concentration s of Factor XIII were prepared. Either 10 ul of a thrombin solution comprising thrombin (700 IU/ml), and Factor XIII (1 IU) or 20 ul of a thrombin solution comprising thrombin (350 IU/ml) and Factor XIII (4 IU) were dispensed into 10 mm hyaluronic acid-coated wells. About 300 μl of the fibrinogen stock solution (24 mg/ml+0.1% HyA) was dispensed over the thrombin solution and a clot was allowed to set at room temperature for about 8 hours. The clot was frozen for 1 hour at −40° C., lyophilized for about 12 hours and seeded with chondrocytes.

The composition of the thrombin solution was varied to produce plasma protein matrices having additional advantageous properties, including enhanced cell attachment, cell proliferation and differentiation. The parameters that may be varied include thrombin concentration, viscosity, volume, temperature and composition. For example, the presence of certain proteins or other viscosity-enhancing agents were added. In all cases the thrombin solution and the plasma protein solutions were cast sequentially, either solution may be cast first. A thrombin solution of about 300 IU/ml about 1500 IU/ml yielded a sponge with good physical and biological properties.

Figure 2A:
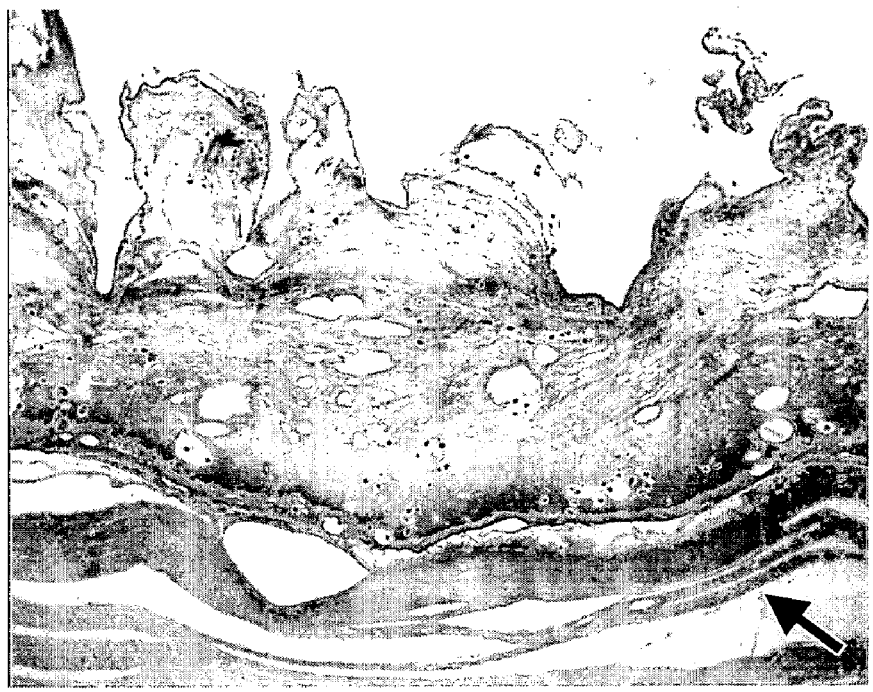
FIG. 2A shows a histological section a plasma protein matrix comprising a collagen matrix on one opposing surface. The arrow indicates the collagen matrix.

Collagen membrane: In certain experiments a collagen membrane (about 0.1 mm thick) comprising crosslinked collagen fibrils was cut to fit a 10 mm well and placed in the bottom of the well. The membrane was impregnated with thrombin solution (864 IU thrombin/ml) and a plasma protein solution (20 mg/ml plasma protein+0.075% hyaluronic acid) was dispensed carefully over the thrombin solution. The clot set for 40 minutes and was frozen and lyophilized. FIG. 2A shows a histological cross section of a matrix prepared layered upon a collagen membrane. The arrow shows the collagen membrane layer.

Figure 2B:
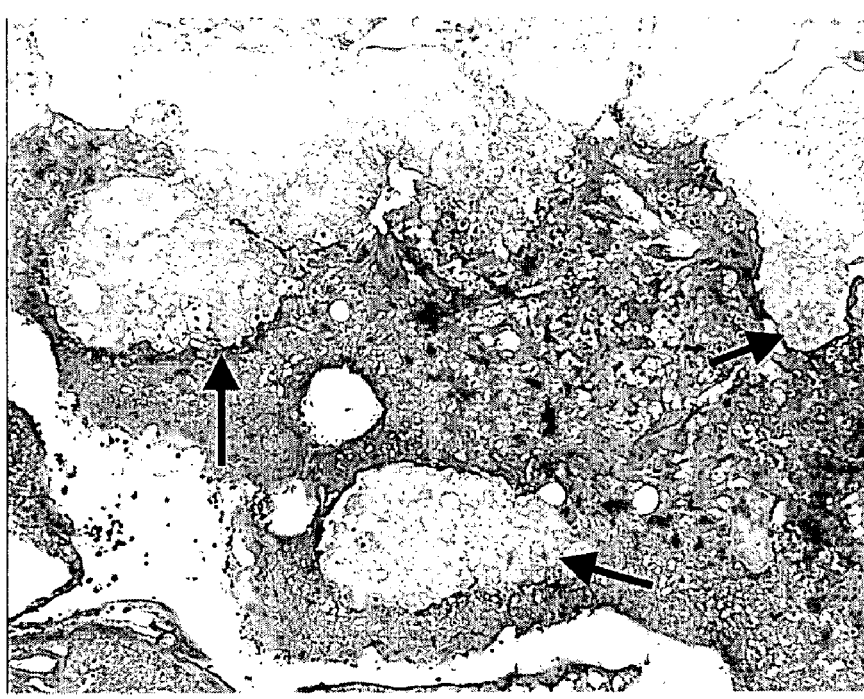
FIG. 2B shows a histological section matrix comprising calcium-phosphate particles. The arrows denote some of the particles.

In other examples a matrix comprising calcium phosphate particles was prepared. A thrombin solution (864 IU/ml+1 gm calcium phosphate particles) was introduced into a 10 mm well. Plasma protein solution (20 mg/ml plasma protein+0.075% hyaluronic acid) was dispensed carefully over the thrombin solution. The clot set for 40 minutes and was frozen and lyophilized. FIG. 2B shows a cross section of a matrix comprising the calcium phosphate particles. The arrows mark the particles.

In some examples, the plasma protein solution (CPP=clottable plasma proteins) and the thrombin solution were cast in a 35 mm diameter well (for example 3000 μl CPP and about 100 μl or about 70 μl thrombin solution). A 6 well ELISA plate was coated with 0.01% hyaluronic acid and was left to dry. In another example, a 48 well ELISA plate (~10 mm diameter wells) was used and about 20 ul or about 50 μl thrombin solution was added to the wells followed by the addition of about 500 ul CPP. The 35 mm diameter clot was formed by leaving the mixture to polymerize at room temperature (~25° C.) for about 1 hour to about 24 hours, followed by freezing, lyophilizing and drying. The matrices were lyophilized at about −70° C. to about −20° C. overnight (10-16 hours) followed by raising the temperature to 20° C. over a period of about an hour prior to releasing the vacuum. The matrices were prepared under sterile conditions.

In some examples, the matrices were prepared using a plasma protein solution comprising certain additives including disaccharides, polysaccharides, GAGS and synthetic polymers. All additives were filtered (0.2 μm) and were added to the plasma protein solution. When hyaluronic acid was incorporated in the matrix, the plasma protein solution and hyaluronic acid solution were incubated together before casting.

In another example, the lyophilized matrix was seeded with cells and a thrombin solution (750 IU/ml) was dispensed onto the surface of the matrix exposed to the lower concentration of thrombin, and allowed to clot. Without wishing to be bound by theory, the additional thrombin interacts with the fibrinogen/fibrin dimers at the surface of the matrix and undergoes clotting to further strengthen the matrix.

For comparison purposes, "mixed" matrices were prepared by premixing the thrombin and plasma protein solutions before casting, freezing and lyophilizing. "Nonmixed" matrices were prepared by dispensing 1 ml of a thrombin solution into a 35 mm well and dispensing 2 ml plasma protein solution over the thrombin solution. A clot was allowed to set and the clot was freeze-dried.

Example 2

Isolation of Partially Purified Plasma Proteins from Whole Plasma

Plasma protein may be prepared from different sources such as fresh plasma, fresh frozen plasma, recombinant proteins and xenogeneic, allogeneic or autologous blood. The fresh frozen plasma may be received from any blood bank or directly from an individual who is to undergo implantation of the matrix (autologous blood plasma) and processed according to the protocol presented in WO 03/007873. Plasminogen-free plasma protein solutions may be prepared according to methods known in the art, including methods taught in PCT patent publications WO 02/095019 and WO 95/25748.

The plasma protein matrices may further comprise endogenous or exogenous blood platelets or platelet supernatant. In a non-limiting example, a method for the isolation of a platelet-enriched plasma is taught in U.S. Pat. No. 6,475, 175. Platelet supernatant is made by exposing isolated platelets (obtained from the Israel blood bank) to thrombin as described (Gruber et al., Clin Oral Implants Res 13:529-535, 2002), collecting the supernatant and adding it to the plasma protein solution prior to sponge formation.

Example 3

Physical and Mechanical Properties of Matrix

In general, matrices for tissue engineering are characterized according to several criteria, including chemical nature, homogeneity, porosity, adhesion, biocompatibility and elasticity, amongst others (Hunziker, Osteoart. Cart., 10:432-465, 2002). Table II in that reference lists several of the properties and the biological basis of these properties.

Figure 3A:
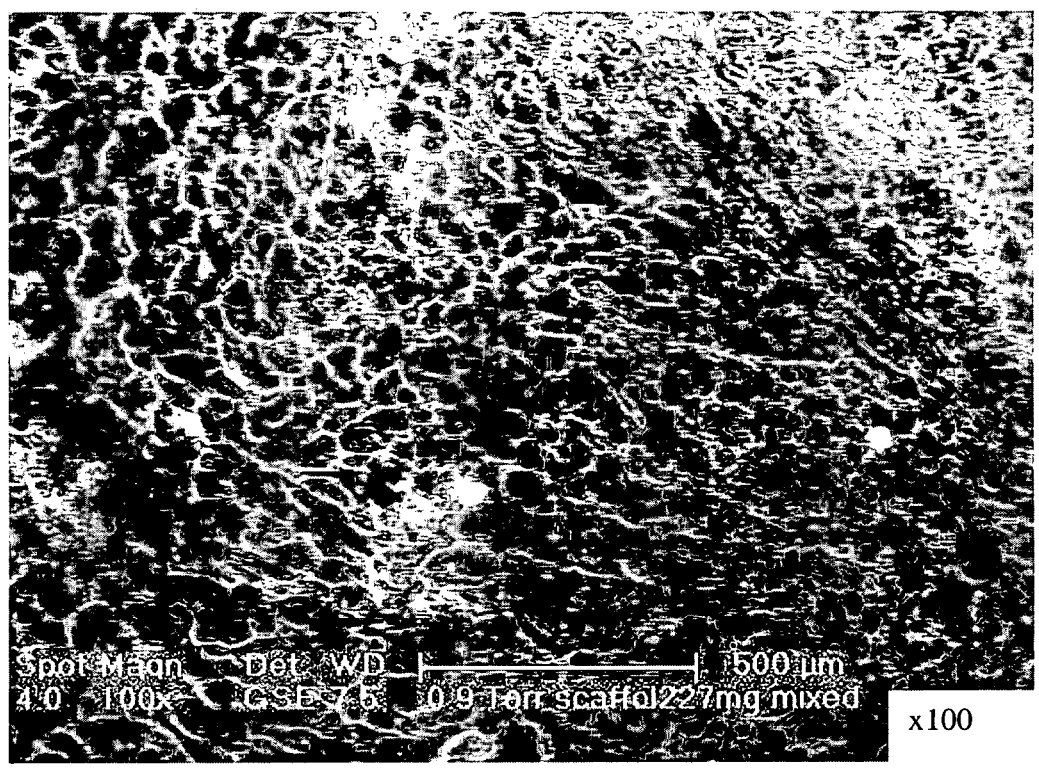
FIGS. 3A and 3B show scanning electron microscope (SEM) photographs of a mixed plasma protein matrix prepared by premixing the thrombin and plasma proteins.
Figure 3B:
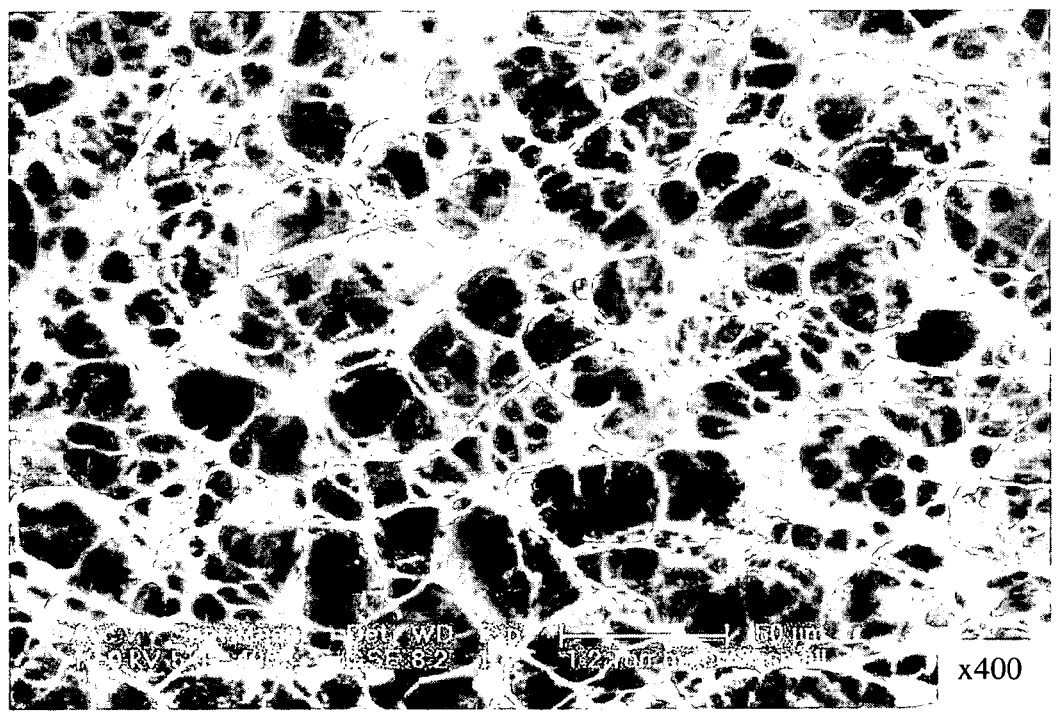
Figure 4A:
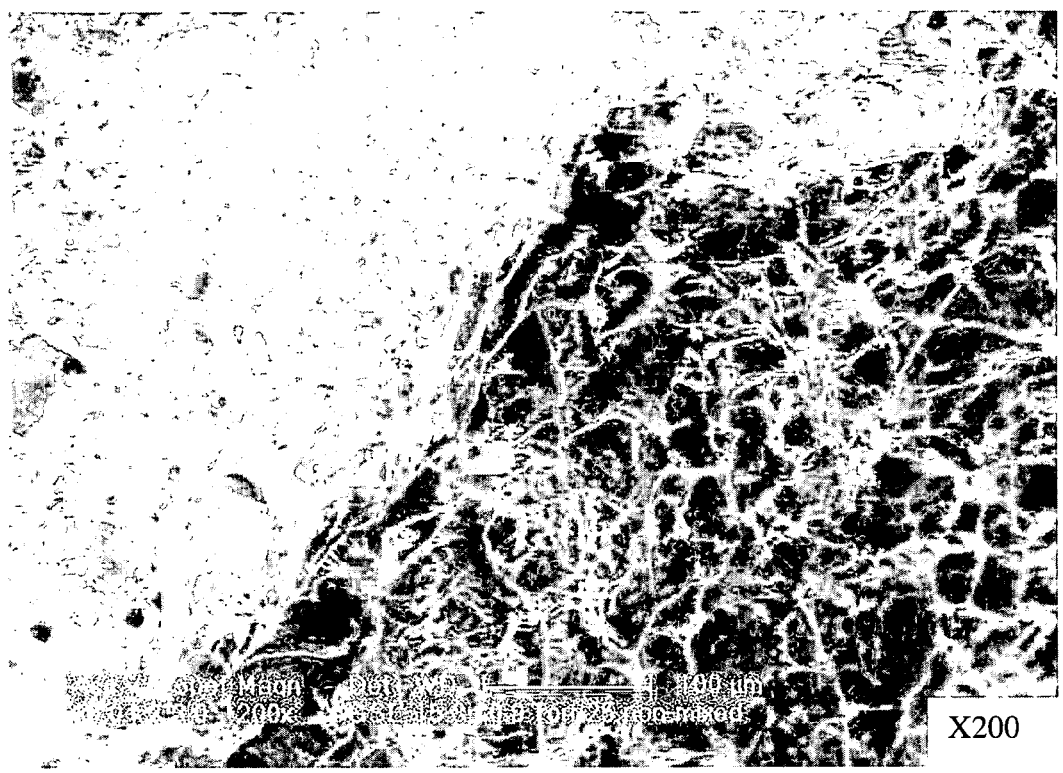
FIGS. 4A-4B show SEM photographs of the nonmixed matrix.
Figure 4B:
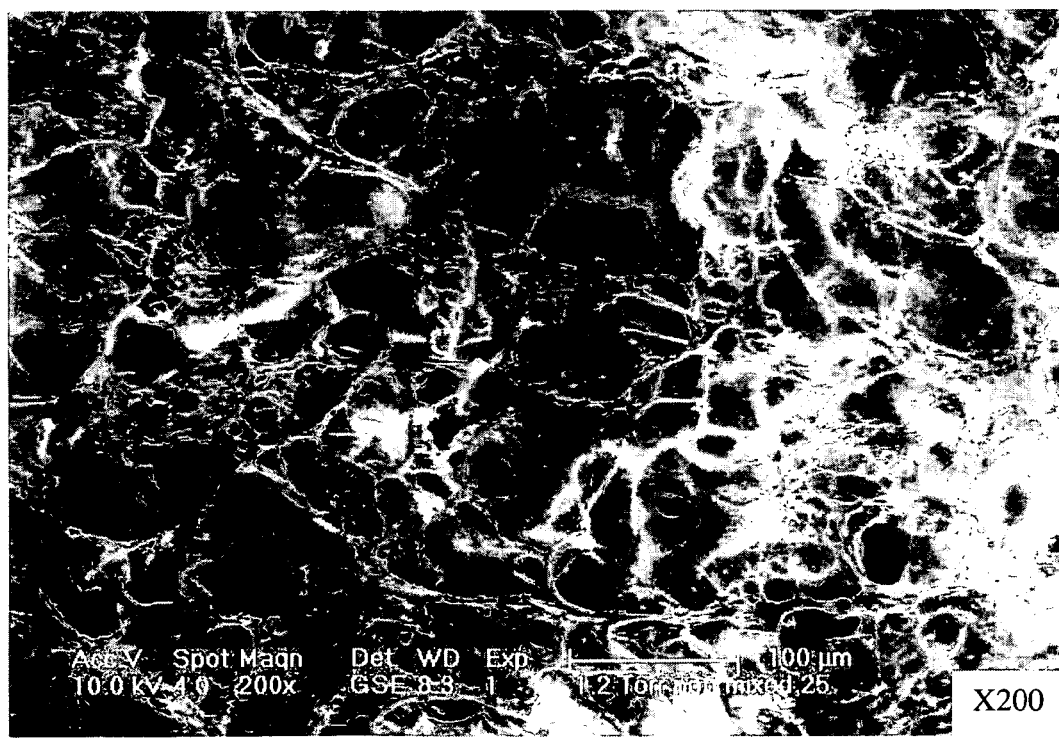
Figure 5A:
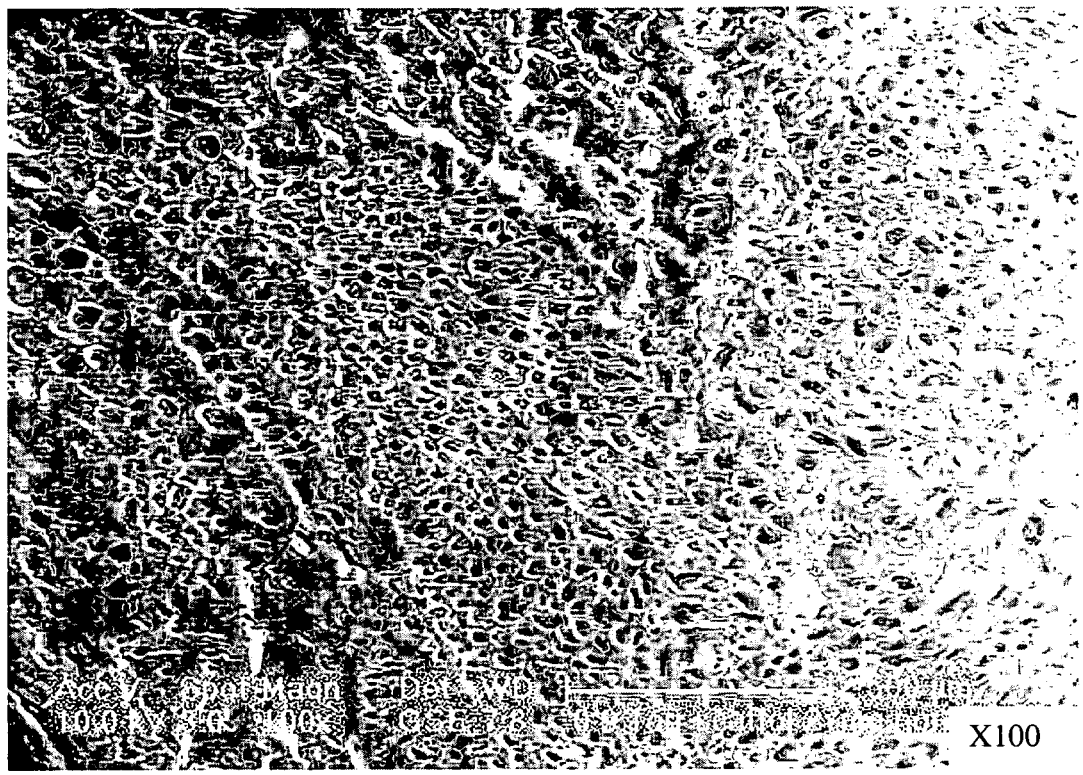
FIG. 5A-5D show SEM photographs of the matrix of the invention.
Figure 5B:
Figure 5C:
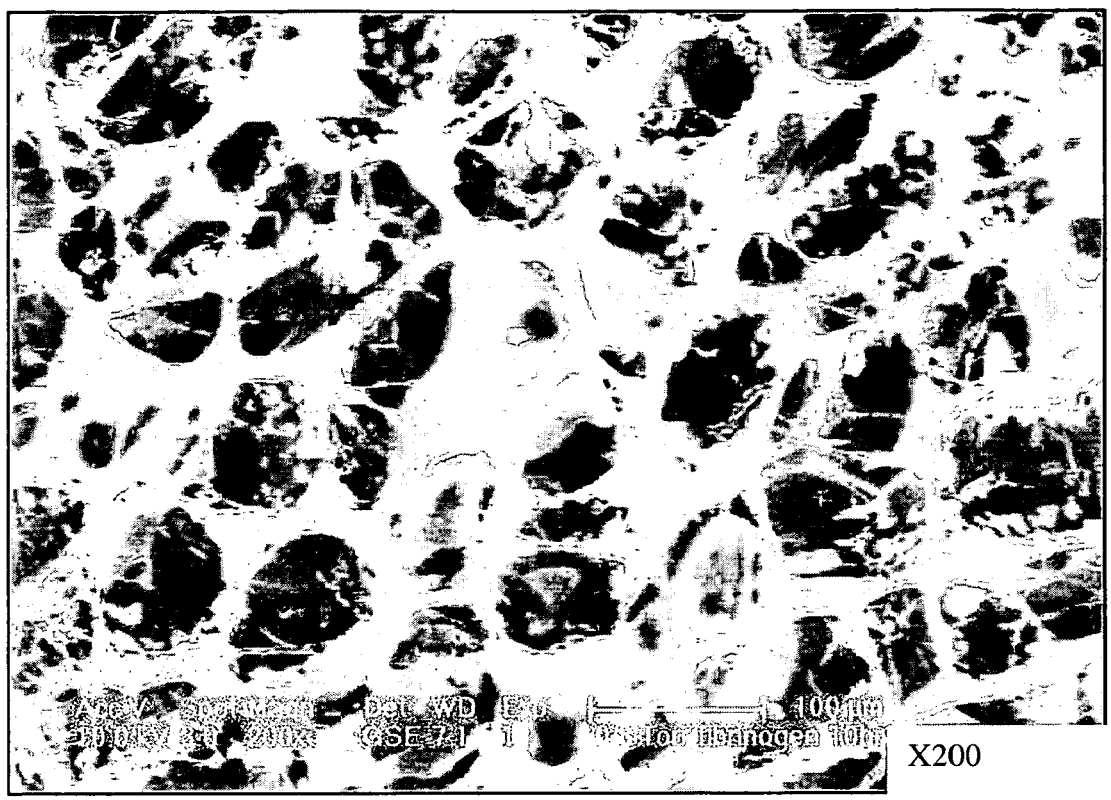
Figure 5D:
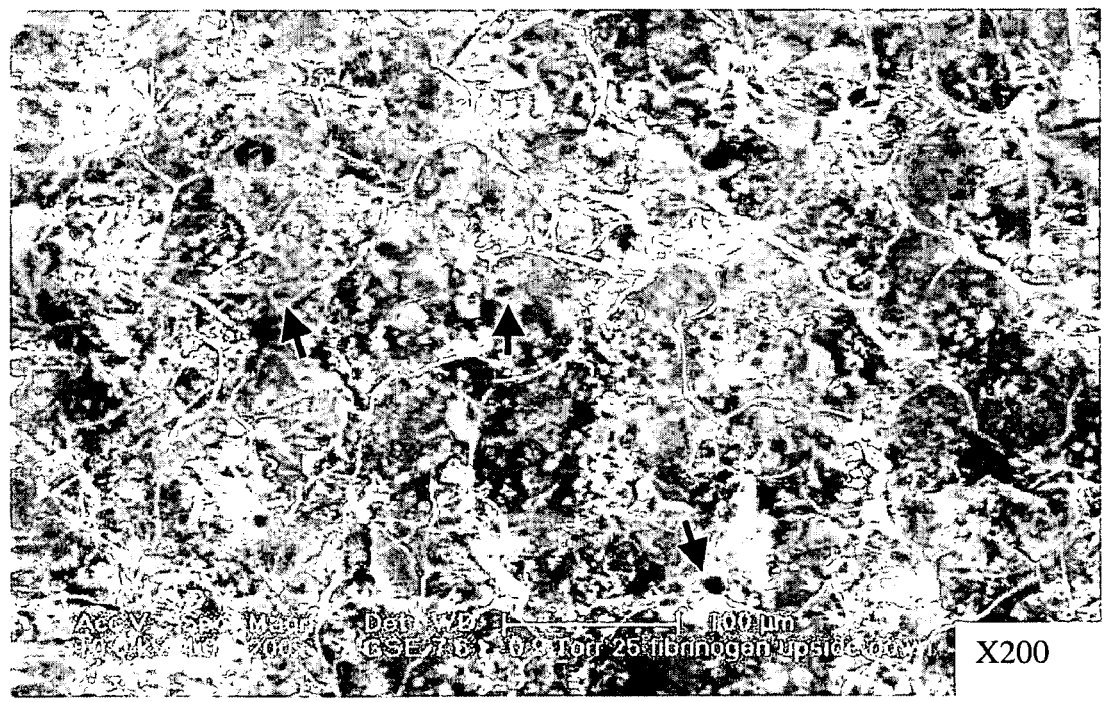

Several of the aforementioned properties have been and will be determined for the matrices of the present invention. Scanning Electron Microscope (SEM) analysis was performed in order to study the ultra structure of the matrices. Comparisons were made between three different types of matrices 1) a "mixed" matrix wherein the thrombin and plasma proteins are mixed prior to casting; 2) a "nonmixed"

matrix where the thrombin and plasma proteins are dispensed sequentially and are present in a ratio of about 1:2, respectively; 3) a "diffusion matrix" wherein the thrombin having a thrombin diffusion gradient. FIGS. 3A and 3B show SEM photos of the upper surface (top) of a premixed matrix (25 mg/ml CPP, 0.1% HyA, 750 IU/ml thrombin). FIGS. 4A and 4B show SEM photos of the "nonmixed" matrices described above. FIG. 4A is a photo of the periphery of the matrix while FIG. 3B is photo of the center upper surface of the matrix. FIGS. 5A and 5B show SEM photo of a surface of the matrix having a lower thrombin concentration (side for cell seeding) in a matrix that was prepared by allowing the clot to set for about 3 hours while FIG. 5C shows the surface of the matrix having a lower thrombin concentration in a matrix that was prepared by allowing the clot to set for about 10 hours. FIG. 5D shows the surface of the matrix having a higher thrombin concentration (3 hour clot setting).

The number of pores per 500 $\mu m^2$ and the average size of the pores (channel openings in cross section) were determined by measuring two axes of the pores from the SEM photos. Values are presented in Table 2, below.

The values are presented as d1×d2, where d1 is one axis and d2 is the axis perpendicular to d1. Comparisons were made between a "nonmixed" matrix having a ratio of plasma proteins to thrombin of about 2:1 (v/v) and a diffusion directed matrix having a ratio of plasma proteins to thrombin of about 30:1 (v/v). Both matrices were prepared from plasma proteins (20 or 25 mg/ml with 0.1% hyaluronic acid) and thrombin (about 750 IU/ml) and were prepared by casting the thrombin solution into a mold followed by casting of the plasma protein solution over the thrombin.

mately 2.5 cm long, 0.5 cm wide; and is fully lyophilized. Deformation represents the elasticity of the sponge, i.e. the amount of pull as measured in millimeters (mm) that may be exerted until the sponge tears. Force is calculated in kilo-Pascal (kPa) and represents the amount of energy required to tear the sponge strips. The thickness of the sponge is taken into consideration when making the calculation.

The amount of residual moisture in the matrix is determined using a variation of Baker's technique. A matrix made with 100 μl of thrombin solution (720 IU/ml) and 3 ml plasma protein solution (24 mg/ml+0.1% HA) was weighed immediately after lyophilization and then every twenty minutes for 2 hours. The matrix was oven dried for 18 hours and the weighing procedure repeated. The weight increase as a function of time (=moisture content increase) after lyophilization and after drying in a 105° C. oven was determined and plotted. The residual moisture of the lyophilized matrix at time zero was extrapolated from the graph, at the intersection of the slope with the y-axis. The residual moisture was calculated as follows: (0.1698-0.1617)*100/0.1698=4.8%.

In its final form, prior to use with cells, the sponge is substantially dry and contains less than 10% residual moisture, more preferably less than 5% residual moisture.

Example 4

Cell Seeding on the Matrix

Different methods of seeding cells onto the sponge may be used. Important to seeding is cell adherence, migratory capacity and proliferation of cells within the matrix. Cells

TABLE 2

Pore number and pore size in different matrices

| | 25 mg/ml nonmixed 3 hr* −70° C. "Top" | 25 mg/ml diffusion 3 h* −70° C. "Top" | 25 mg/ml diffusion 3 h* −70° C. "bottom" | 24 mg/ml diffusion 10 h* −40° C. "Top" | 24 mg/ml diffusion 10 h* −40° C. "bottom" | 24 mg/ml diffusion 10 h* −70° C. "Top" | 24 mg/ml diffusion+ 10 h* −70° C. "bottom" |
|---|---|---|---|---|---|---|---|
| Avr. no. pores (per 500 $\mu m^2$) | 15 | 53 | 21 | 44 | 26 | 49 | 33 |
| Average pore size (μm) | 22 × 22 | 32 × 40 | 10 × 9 | 33 × 34 | 14 × 16 | 21 × 22 | 9 × 9 |

*number of hours clot allowed to set before freeze-drying
+thrombin solution comprises albumin, collagen and elastin
temperature refers to freeze-drying temperature
non-mixed refers to a matrix as defined and described in Example 1a.
Diffusion refers to the matrix of the invention prepared as described in Example 1.
"top" refers to the surface of the sponge having a lower thrombin concentration (the side used for cell seeding) while
"bottom" refers to the opposing surface of the sponge having a higher thrombin concentration.

The present invention provides a matrix having a large number of channel openings in addition to pores having a larger size. These characteristics allow for better distribution and dispersion of the cells throughout the matrix and are beneficial for cell attachment, proliferation and or differentiation.

Mechanical property measurements are performed, for example, using a Chatillon TCD200 machine with a digital force gauge DF12. Each plasma protein sponge is approximay be suspended in medium, PBS, or any compatible buffer alone or in the presence of serum and or bioactive agents. Cells may be seeded by placing a drop of liquid containing cells on the sponge and allowing the cells to adsorb into the sponge. Alternatively, the cells in the liquid may be absorbed into the sponge by placing the sponge in a container holding a suspension of cells. Other methods including spray seeding have also been shown to be effective.

One particular advantage of the matrix of the present invention is the high level of cell viability and excellent cell distribution throughout the matrix.

Materials and Methods:

Matrices comprising different concentrations of plasma proteins and thrombin were tested. Varying numbers of cells were seeded on the sponge. In one assay, $7 \times 10^6$ chondrocytes were spray seeded on 10 mm diameter matrices (24 mg/ml CPP, 0.1% HyA, thrombin solution (about 720 IU/ml) and viscosity-enhancing agents).

Figure 6:
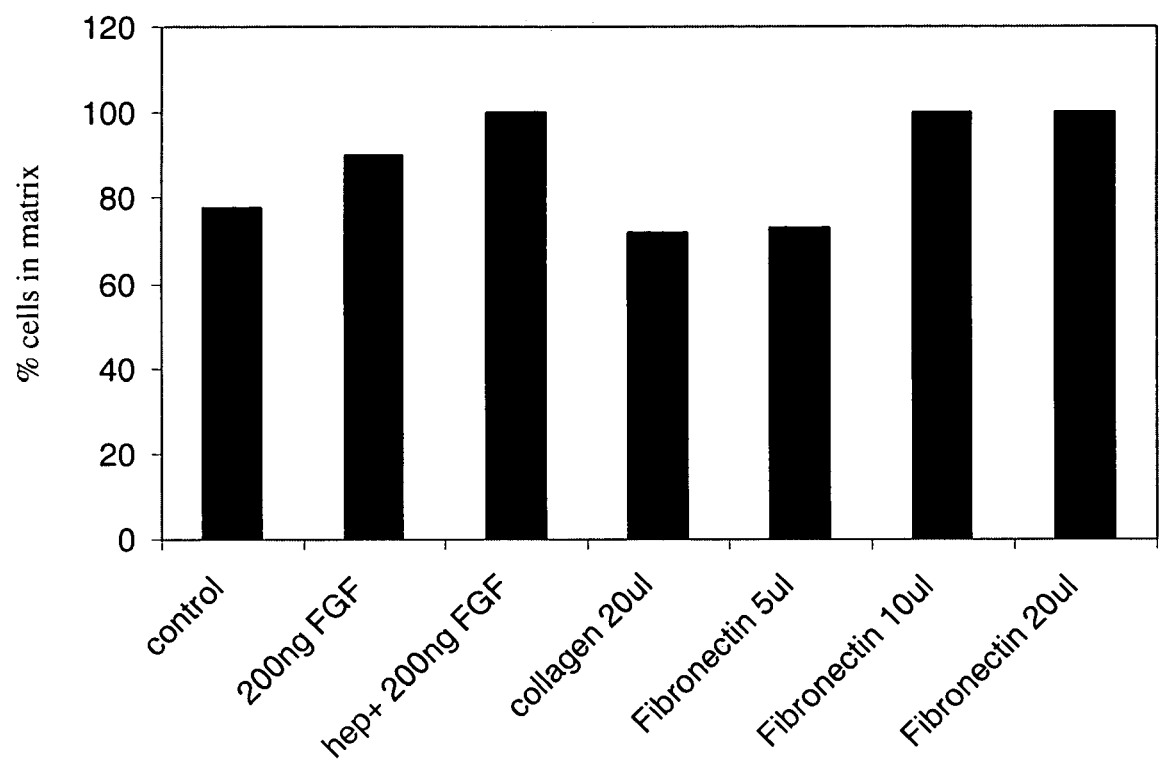
FIG. 6 shows a graph of cell survival in several matrices of the invention following three day incubation.

Following a three-day incubation for the seeded matrices, some of the matrices were collagenase degraded and cells counted following trypan blue staining. The graph in FIG. 6 shows the percentage of live cells remaining in the different matrices of the present invention following three-day incubation. Control refers to the matrix per se devoid of agents in the thrombin. 200 ng FGF refers to 200 ng/ml FGF2 that was added to the thrombin solution before formation of the matrix. Hep+200 ng FGF refers to heparin (200 ng/ml) present in the plasma protein solution and 200 ng/ml FGF present in the thrombin solution prior. The other columns refer to the amounts of collagen I and fibronectin present in the thrombin solution. The number of live cells remaining in the matrices is overall very high (>70%).

Samples of the cell-bearing sponges or matrices, were paraffin-embedded and sections prepared using a microtome. The histological sections are further stained using different biological stains including hematoxylin and eosin (H&E), toluidine blue and fast red, Masson's trichrome stain and others. All sponges exhibited similar cell distribution, with live cells present throughout all layers of the sponge.

Example 5

In Vitro Degradation Assay

The in vitro degradation assay is carried out to determine the rate of degradation of the sponge. Without wishing to bound to theory, the greater the extent of cross-linking in a fibrin matrix the slower its degradation rate. The assay is performed in the following manner:

Five sponges prepared in 96 well plates (5 mm diameter) are placed in 48 well plates and 750 ul of 10M urea was added to cover the sponges. Samples of 20 ul are collected from each well at the following points: 1, 2, 3, 4, 5, 8 minutes, 10 minutes, 30 minutes, 1 hrs. Protein from each sample is measured in a standard Bradford assay.

Example 6

Release of Bioactive Agents from the Matrix

For certain applications, sustained release of a bioactive agent such as a growth factor may be desirable. The incorporation and release of growth factors from the matrix of the invention was assessed in vitro and may be assessed in vivo using radiolabeled or tagged growth factors, for example fluorescent-labeled, alkaline phosphatase labeled or horseradish peroxidase-labeled growth factor. The fraction and rate of released agent is measured by following the radioactivity, fluorescence, enzymatic activity or other attributes of the tag. Similarly, sustained release of enzymes from the matrix may be determined by analyzing enzymatic activity into the microenvironment in an in vitro or in vivo assay.

For example, sponges comprising a heparin binding growth factor such as FGF2 may be prepared in one of several ways: FGF2 is bound to heparin and the mixture is added to either the thrombin solution or to the plasma protein solution ab initio. In another non-limiting example, each component (heparin and a heparin binding growth factor) is added separately to the individual solutions: for example, heparin is added to the plasma protein solution while FGF2 is added to the thrombin solution. Sponges are cast and FGF2 release is determined in an FDCP assay, vide supra.

FDCP Assay: The FDCP cell line is a murine immortalized, interleukin 3-dependent cell line of myelocytic bone marrow origin that does not express endogenous FGF Receptors (FGFR). Upon transfection with FGFR (FGFR1-4) cDNA, the FDCP cell line exhibited a dose-dependent proliferative response to FGF that can replace the dependence on IL-3. FGFR transfected FDCP cells can therefore been used to screen for FGFR signaling. FDCP cells response to various ligands is quantitated by a cell proliferation assay with XTT reagent (Cell Proliferation Kit, Biological Industries Co.). The assay measures the capability of mitochondrial enzymes to reduce tetrazolium salts into a colorigenic compound, which can be quantitated and is indicative of cell viability.

Example 7

Chondrocyte Isolation and Culturing

Reagents:

Collagenase Type 2; Worthington Biochemical Corp. (Cat. #: 4147)

Stock solution: 1700 units/ml in medium (in MEM)

Dulbecco's MEM (DMEM) (Gibco BRL, cat. no. 41965)

Minimal Essential Medium (MEM) Gibco BRL (cat: 21090-022)

Fetal Bovine Serum (FBS); Gibco BRL (cat: 16000-044)

L-Glutamine Solution; Gibco BRL (cat: 25030-024)

Complete medium: MEM supplemented with 10% fetal calf serum (FCS), 2 mM L-Glutamine and 100 U/ml penicillin, 100 μg/ml streptomycin Preparation of Implants for Treatment of Articular Cartilage Defects The sponge of the present invention may be used as a cell-bearing scaffold for tissue repair and regeneration. In one embodiment, cells are cultured on the sponge in vitro, prior to implantation. In another embodiment, the sponge is seeded with cells before implantation. In yet another embodiment the matrix is implanted and cells are seeded on or in the vicinity of the matrix, in situ.

Biopsies from human or porcine articular cartilage were wiped with 70% alcohol, and placed in laminar flow hood. The tissue was diced to approximately 1-2 mm pieces, washed aseptically with PBS and placed in a new tube containing 2 ml DMEM medium and 2 ml collagenase solution. The mixture was shaken gently in a 37° C. incubator over night. When most of the sample was digested, the suspension was poured through sterile gauze to remove matrix debris and undigested material. The filtrate was centrifuged and washed twice in DMEM to remove residual enzyme.

The number of cells was determined by a hemocytometer and viability was determined by Trypan blue exclusion. The cells were plated in 25 cm$^2$ or 75 cm$^2$ tissue culture flasks in human or fetal calf serum and culture medium at a concentration of about $3 \times 10^5$ cells/ml (25 cm$^2$ flask) or $1 \times 10^6$ cells/ml (75 cm$^2$ flask). Flasks were incubated at 37° C., 5%

$CO_2$ atmosphere and 95% humidity. The medium was changed every three to four days. The cells reached confluency after about one week incubation.

Figure 7A:
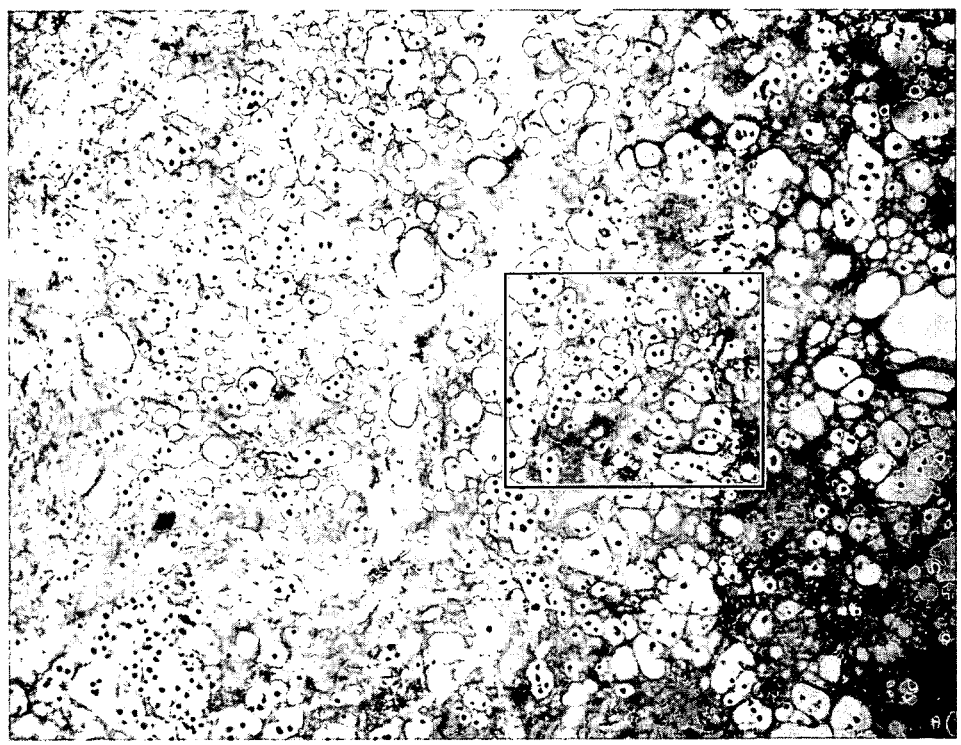
FIGS. 7A and 7B show cross sections of a matrix of the invention, seeded with chondrocytes.
Figure 7B:
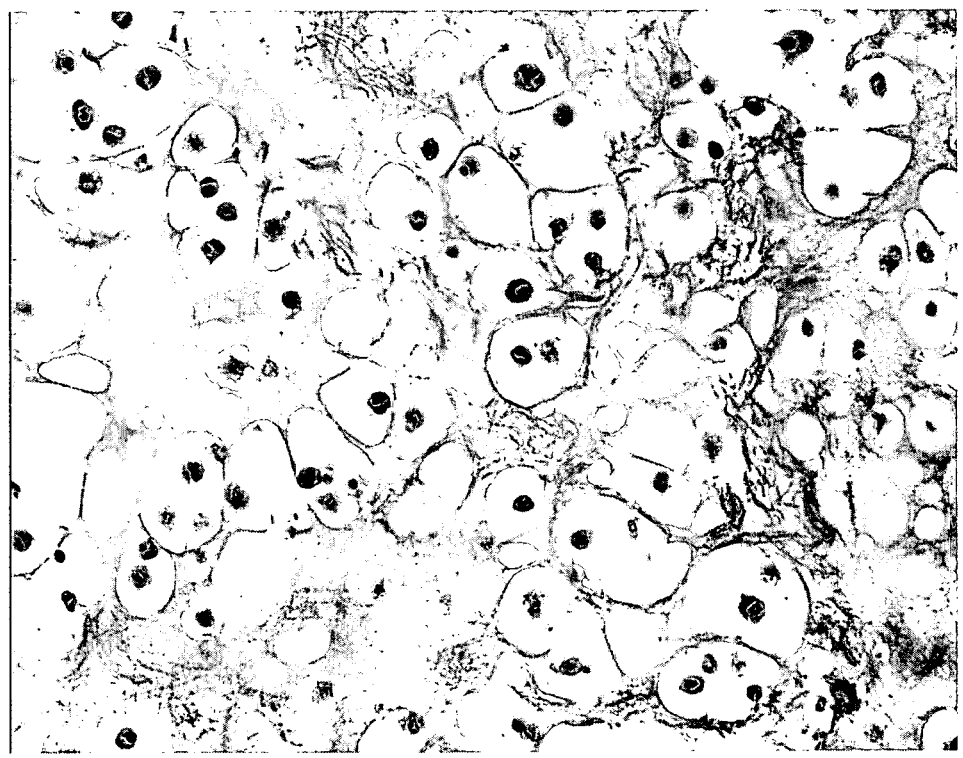

At confluency, the cell medium was replaced with 3 ml of a trypsin-EDTA solution. Thirty ml MEM+FBS was added, the solution was centrifuged at 800 g for 10 minutes. The pellet was gently dispersed and the cells were counted. To create a cell-bearing matrix, $10^2$-$10^6$ cells were seeded on a fibrin scaffold of 9 mm in diameter and a thickness of 2 mm (approximately 0.2 $cm^3$) or 35 mm diameter and about 2.5 mm thick (~1.2 $cm^3$). The matrices were incubated at 37° C. for about 1 hour and 1 ml of fresh medium was added to each. The medium was replaced with fresh medium and the matrices were incubated for several days to several weeks before being analyzed for cell proliferation, cell differentiation and histology. FIGS. 7A and 7B show histological cross sections of chondrocyte-bearing matrices.

The cells grown on the matrices express chondrocyte differentiation markers including glycosaminoglycan (GAG) production. GAGs may be identified by staining tissue or matrix sections with Alcian blue and quantitated using the DMB Dye (3,3'-dimethoxybenzidine dihydrochloride) method. Extracellular matrix proteins may also be identified by staining with toluidine blue and fast red or by RT-PCR analysis of RNA.

In another examples, spinal disc cartilage was biopsied and the cells cultured for implantation on a matrix.

Example 8

Hepatocyte Culturing

To determine the capacity of the plasma protein matrix to support cell growth for tissue regeneration and repair, primary rat liver hepatocytes were cultured on the matrix.

Primary rat hepatocytes were isolated by perfusing the rat liver. Briefly, a veinflon was inserted in the portal vein of laparotomized rats anesthetized with Nembutal. The liver was then perfused with a 5 mM EGTA solution in Lefferts buffer (10 mM Hepes, 3 mM KCl, 130 mM NaCl, 1 mM $NaH_2PO_4$.—$H_2O$, 10 mM D-Glucose, pH 7.2) using a peristaltic pump at a speed of 12 ml/min for a total of 4 minutes. The liver was washed for 2 minutes with Lefferts buffer, followed by 15 minutes perfusion with 0.35 mg/ml collagenase Type 1 (333 U/mg, Worthington Biochemical Corporation, NJ, USA) in Lefferts buffer with 0.027% $CaCl_2$. The liver was gently placed in the HDM medium described below and hepatocytes were released from the Glisson capsule using two scalpel blades. The cells were washed by centrifugation at 50 g twice and suspended at the desired cell concentration.

Figure 8A:
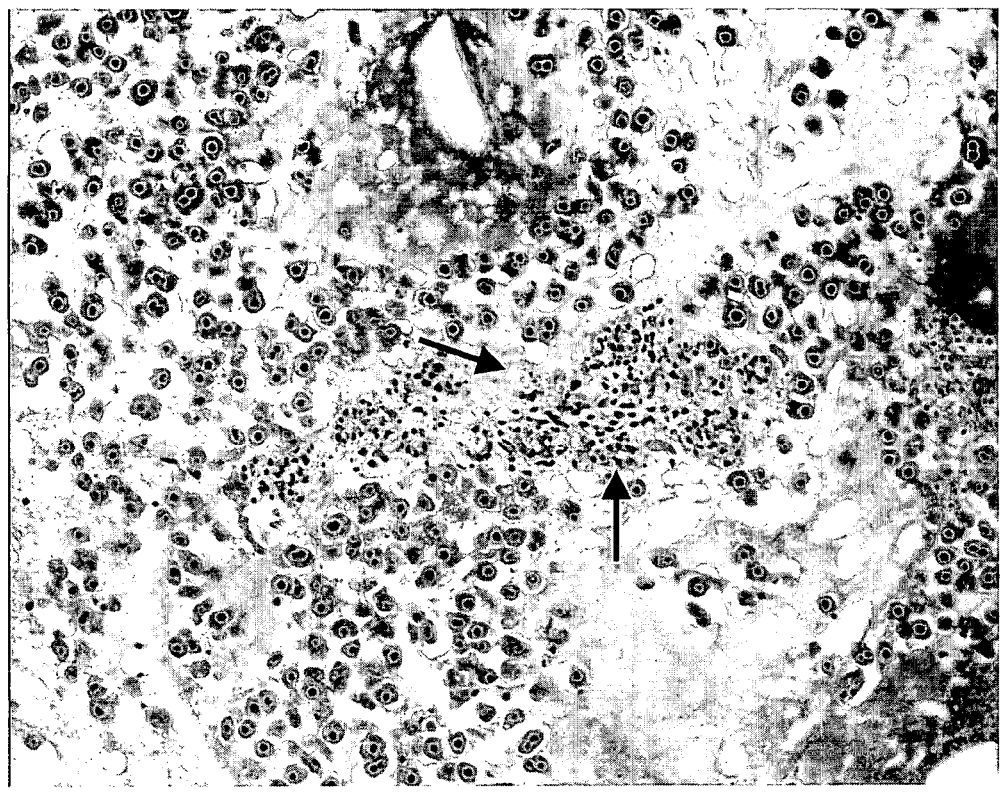
FIGS. 8A and 8B show cross sections of a cell-bearing matrix of the invention, seeded with rat hepatocytes.
Figure 8B:
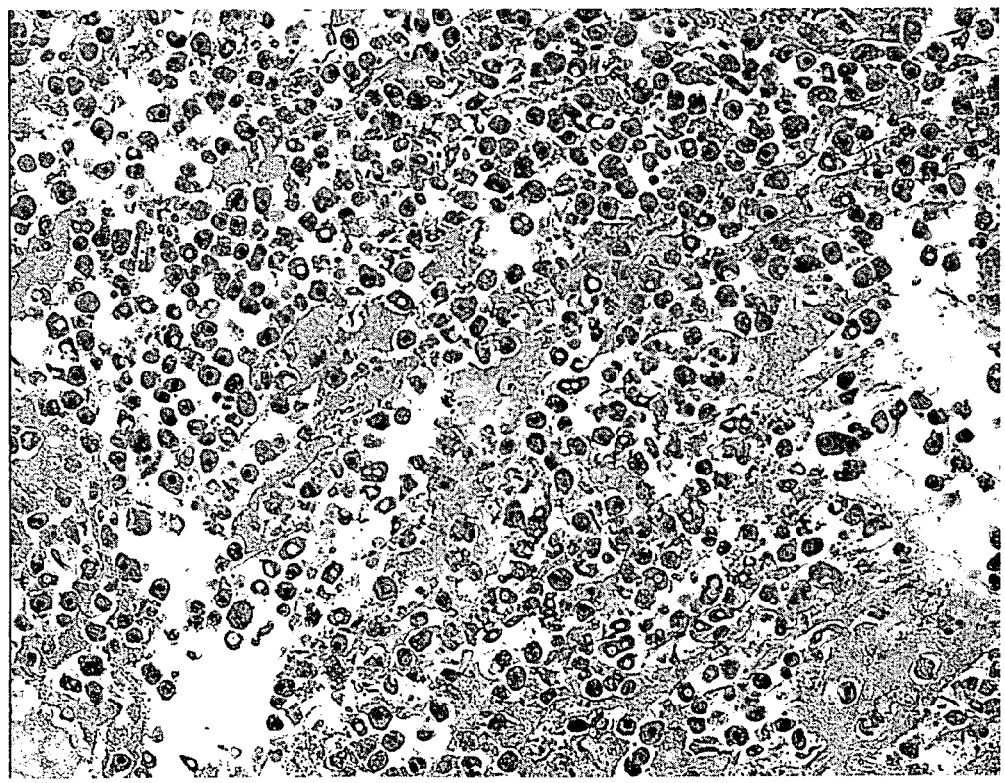

Ten mm or 35 mm diameter sponges comprising plasma proteins (24 mg protein/ml), 0.1% hyaluronic acid and 720 IU thrombin/ml were prepared. Approximately $6.6 \times 10^5$ primary hepatocytes were seeded on the sponges in HDM (hormonally defined medium) without serum and allowed to incubate for three days at which histological samples were made and stained with H&E. FIG. 8A shows a representative section of a sponge comprising hepatocytes, following a three day incubation. Note the good dispersion of cells throughout the matrix and the presence of cells maintaining their hepatic characteristics. The arrows denote bile duct cells. FIG. 8B shows the section of a matrix that had been seeded with hepatocytes and incubated 14 days. The cells retain good morphology as the matrix begins to degrade.

Example 9

Cell Proliferation Assay

Proliferation of the cartilage cells on the matrix of the invention was quantitated by one of two methods, CyQUANT® (Molecular Probes) or XTT reagent (Biological Industries, Co.). The matrix was dissolved in collagenase or other enzymes and the cells collected by centrifugation and analyzed according to directions provided by the manufacturers.

Example 10

Ectopic Cartilage Formation in Nude Mice

The assay is designed to determine the ability of isolated chondrocytes to create neocartilage in an ectopic site, and to determine the quality of this cartilage compared to natural cartilage. Human and porcine chondrocytes seeded on a matrices of the invention are used to induce ectopic cartilage on the backs of nude mice.

Treatment arms: The study groups included different amounts of cells seeded onto the plasma protein matrix substantially devoid of plasminogen. Human or porcine chondrocytes were seeded onto a plasma protein sponge from a 96 well plate (~65 ul). The control group consisted of matrices implanted without cells.

Seeding: Sponges were seeded with human or porcine chondrocytes ($10^5$-$10^6$/20 ul culture medium in a 96 well plate and incubated at 37° C. for 1 hour. Culture medium was added to the well and the sponge incubated 24-48 hours. The sponge was placed into subcutaneous incisions made on the back of nude mice.

Implantation procedure: Animals are anesthetized using ketamine-xylazine. Back skin is shaven and cleaned using alcohol. Two incisions, are made on each side of the back, parallel to the spine. A subcutaneous pocket or a pocket in the muscle fascia is made from each incision using blunt dissection. The sponges are implanted in the pockets according to treatment arms and the skin is closed with single suture. Each treatment is repeated 5 times. and each mouse is implanted with 4 sponges.

The treatment arms are presented in table 3 herein below.

TABLE 3

| | Ectopic Cartilage Experimental Setup | | | | |
|---|---|---|---|---|---|
| Mouse No. | Left proximal | Left distal | Right proximal | Right distal | Tagging |
| 1 | $10^5$ Human | $10^6$ Human | $10^5$ Porcine | $10^6$ Porcine | No tag |
| 2 | $10^6$ Human | $10^5$ Human | $1 \times 10^6$ Porcine | w/o cells | 1 Rt ear |
| 3 | $10^6$ Porcine | $10^5$ Porcine | $10^5$ Human | $10^6$ Human | 1 Lt ear |
| 4 | $10^5$ Porcine | w/o cells | $1 \times 10^6$ Human | $10^5$ Human | 2 Rt ear |
| 5 | $10^6$ Human | $10^6$ Porcine | Sponge w/o cells | $10^5$ Human | 2 Lt ear |
| 6 | w/o cells | w/o cells | $10^6$ Porcine | $10^5$ Porcine | RT + LT |

Induced cartilage formation evaluation: One or four weeks post implantation the mice are sacrificed and the implants with their surrounding tissue retrieved and prepared for histology evaluation. The microscopically assessment consists of a complete morphological description of the implant. Additional analyses include H&E staining safranin O, alcian blue and anti-collagen type II staining.

Example 11

Sheep Model of Cartilage Repair

This study was designed to evaluate the capacity of the chondrocyte embedded matrix of the invention to repair cartilage in a large animal model. Sheep weighing about 60-80 kg each are chosen. Several of the animals will undergo chondrocyte harvesting procedure prior to implantation. The harvested chondrocytes are expanded and seeded onto plasma protein matrices prepared from human plasma. An exemplary study design is shown below.

Experimental Setup

| # Sheep | Treatment |
| --- | --- |
| 1A-4A | untreated |
| 1B-4B | microfracture |
| 1C-4C | Matrix (20 mg/ml) |
| 5C-8C | Matrix (24 mg/ml) |
| 9C-12C | Matrix (28 mg/ml) |
| 1D-4D | Cell bearing Matrix (20 mg/ml) |
| 5D-8D | Cell bearing Matrix (24 mg/ml) |
| 9D-12D | Cell bearing Matrix (28 mg/ml) |

The experiments are performed in accordance with the principles of the local laws for Animal Experiments. The animals are examined for evidence of disease or lameness. Acceptability into the study is contingent on being disease free, clinically sound, and no history of prior use. Osteoarthritis is excluded by a preoperative X-ray. The animals are conditioned for an appropriate period. A unique number tattoo and ear tag identified each animal. Animals are assigned to the treatment groups by random allocation of identification numbers.

Group A. Untreated defects: 4 animals (8 defects) the chondral defects are left untreated.

Group B. Microfracture: 4 animals (8 defects) microfracture is performed without further treatment.

Group C Plasma protein matrix alone: Plasma protein matrices, different concentrations, comprising 0.01% HA are implanted in 12 sheep (1C-12C).

Group D Cell bearing plasma protein matrix: Chondrocyte bearing matrices comprising cross HA are implanted in 12 sheep (1D-12D).

The attending veterinarian will perform a clinical diagnosis and treatment on the animal if it shows signs of illness. Bodyweight measurements are taken once during the quarantine period, prior to surgery (Day 0) and at the end of the study (Day 112).

Operation: The left knee joint is sterilely draped and opened by an anteromedial approach under general anaesthesia. The medial condyle is exposed, and small pieces of cartilage were harvested from the low weight bearing surfaces of the trochlea and intercondylar notch. The cartilage is cut superficially with a scalpel to avoid bleeding. The wound closure is performed in layers. An external plaster fixation for stifle joint and ankle is applied for five days and cage activity limited to reduce joint loading in order to prevent dislodgement of the patella. The tissue specimen is diced and washed under sterile conditions and the cells isolated by collagenase following a standard digestion protocol. The cells were plated in 75 ml flasks (Corning) and incubated at 37° C. Changing of media is performed every other day. After 2-3 weeks about 200,000 ($2 \times 10^5$) cells were seeded on the plasma [protein matrices and cultivated for 3-4 days in 6-well plates. The cell-bearing matrices are sterilely transferred to the operation room. The medial condyle of the right knee of the same sheep is exposed. Using a 4.5-mm punch (Smith & Nephew), two defects, 1 and 2.5 cm distal from the intercondylar notch, are made in the medial condyle of the femur. The defects are outlined with the dermal punch down to the subchondral bone and the cartilage is removed with small curettes. The matrices are fixed into place using fibrin glue.

After treatment of the defect, bleeding points of the capsule are stopped by cauterization and wound closure performed in layers. The external plaster fixation is applied for another five days and cage activity limited to reduce joint loading in order to prevent dislodgment of the graft and reparative tissue. After removal of the plaster, the sheep are given unrestricted activity in runs, and fed with a balanced nutrition twice a day. Until the second postoperative day 2 g cefazolin is administered thrice daily.

Necropsy: Animals will be humanely sacrificed at 16 weeks postoperatively according to the guidelines set forth by the AVMA Panel on Euthanasia.

Gross evaluation and sample collection is performed. The articulating surfaces opposing the defect sites are examined for any abnormal joint surface. Additionally, gross evaluations of the knee joints are made to determine the cartilage repair based on previous scoring criteria listed in table 4 below. Femora, patellae, synovium, and popliteal lymph nodes shall be harvested and placed into appropriately labeled containers. Immediately following tissue harvest, gross morphological examination of the cartilage surface was performed and photographic records made of each specimen.

TABLE 4

Scoring Criteria for Gross Morphological Evaluations

| Characteristic | Grading | Score |
| --- | --- | --- |
| Edge Integration (new tissue relative to native cartilage) | Full | 2 |
|  | Partial | 1 |
|  | None | 0 |
| Smoothness of the cartilage surface | Smooth | 2 |
|  | Intermediate | 1 |
|  | Rough | 0 |
| Cartilage surface, degree of filling | Flush | 2 |
|  | Slight depression | 1 |
|  | Depressed/overgrown | 0 |
| Color of cartilage, opacity or translucency of the neocartilage | Transparent | 2 |
|  | Translucent | 1 |
|  | Opaque | 0 |

Histology and Histological Evaluation: The knees are opened under sterile conditions and a culture swab obtained. Synovium is documented macroscopically and the defects are photographed and the joint grossly examined. The distal femur is removed and placed in 10% neutral buffered formalin for 12 hours. Areas of trochlea containing the defects and the harvest sites are dissected and placed into 10% formalin for 4 days. The specimens are subsequently placed into a decalcification solution [100 g Tritriplex (Epignost, Austria) and 33 g Tris-hydroxymethylene-amnomethane (Merck Eurolab, Belgium) per liter] for two to four days at room temperature. The decalcified specimens are embedded in paraffin and cut in a microtome to 5 μm thick sections.

Sections are stained with hematoxylin and eosin (H&E), safranin O/Fast Green, alcian blue and azan for evaluation of tissue types. Immunohistochemistry with antibodies for type I and type II collagens is performed according to a standard ABC protocol using HRP conjugated antibodies. Normal healthy ovine cartilage and tendon served as controls.

Light microscopy is performed on a Vanox Olympus research microscope implementing a histomorphometric method to determine the percentage of selected tissue types (analySiS). Multiple serial transverse histological sections from the middle portion of the defect are evaluated. The filling of the defect is determined as an area percentage of reparative tissue in the defect, based on the cross-sectional area in a sagittal plane through the center of the lesion. The area of the defect, of the filling, height and base of the defect, and tissue type are evaluated. The tissue types are characterized as follows: 1. fibrous tissue 2. transitional tissue 3. hyaline tissue and 4. articular cartilage. Semiquantitative analysis of the defect and adjacent tissue are done according standard scores adapted from O'Driscoll, Pineda and Frenkel.

Example 12

Human Clinical Trial

A feasibility study to evaluate the safety and performance of the plasma protein matrices of the invention in the treatment of chronic cartilage defects of the femoral condyle will be submitted to the authorities.

A phase I, non-randomized, open label, safety study using a plasma protein matrix or a cell-bearing plasma protein matrix of the present invention and autologous chondrocyte in patients is performed. Patients meeting the entrance criteria will undergo an arthroscopic procedure to confirm diagnosis and to harvest a biopsy for the growth of chondrocytes for future transplantation. Three to six weeks following cell harvest, patients will be hospitalized for surgery. After surgery, patients will be monitored for safety as follows: during 5-7 days hospitalization; after discharge at week 2 and week 6, and performance evaluation at week 12, month 6, and month 12.

The primary endpoint is to evaluate the safety the matrix serves as a scaffold for the seeding and transplantation of autologous chondrocytes in the treatment of a chronic cartilage condyle lesion. The secondary endpoint is to evaluate the performance of a cell-bearing matrix in restoring function, as measured by an improvement in: MRI scores, quality of life questionnaire, joint function score. The safety parameters will include vital signs, serum chemistry, hematology and systemic and local adverse events.

Example 13

One-Step Procedure for Treating Damaged Cartilage

Autologous chondrocyte transplantation (ACT) has proven clinically effective in restoring hyaline-like cartilage to isolated chondral defects of the knee. The technique requires three major steps: 1) diagnostic arthroscopy and biopsy of healthy cartilage, 2) cell cultivation, 3) injection of cultured chondrocytes into the lesion under a periosteal flap, which is taken from the tibia and sutured over the lesion.

The disadvantages of ACT include the need for two separate surgical procedures, the requirement for a second site surgery to isolate a periosteal flap and the tendency for cartilage overgrowth due to the presence of the flap. The procedure has gained limited acceptance in the orthopedic community due to the laborious surgical procedure and lengthy rehabilitation. An improved variation provides implantation of a matrix (autologous or allogeneic) of the present invention in a less traumatic method such a hemiarthrotomy or arthroscopy and avoiding the extra surgical step and trauma associated with the periosteal flap. Additionally, an individual may donate plasma several days prior to the surgery for preparation of an autologous matrix.

Kit: A kit comprising the components for practicing the method of the invention, will allow for the convenient practice of the method of the invention in a surgical setting. In one embodiment, a kit will provide sterile components suitable for use in the surgical setting including, sterile solutions (saline, enzymes) a cell-free or cell-bearing matrix suitable for supporting autologous chondrocytes that are to be implanted into an articular joint surface defect and instructions for use.

Example 14

Bone Repair Model

The plasma protein matrix of the present invention is useful for the treatment of bone defects including osteotomy, particularly in non-weight bearing regions of the skeleton. Suitable animal models include a 4-6 mm osteotomy in the mid ulna bone of rabbits. The ulna is chosen because it is only slightly weight-bearing and allows the creation of a bone defect without requiring a cast or other immobilization treatment. The surgical procedure includes standard anesthesia protocols. A sponge of the invention is placed into the gap area in each limb and the fracture is closed. Animals are treated with analgesic for 3 days post operation. The duration of the experiment is 6 weeks.

Healing time and quality assessment: X-ray grading provides fracture healing status assessment. Rabbits are X-rayed every other week for 5-6 weeks after surgery. X-rays are scored by two orthopedic surgeons in a blinded manner according to a standard grading scale protocol. At the end of the experiment, rabbits are sacrificed and fracture area is sent for histological and mechanical strength evaluation. Histology is scored by a pathologist using standard staining methods, using hematoxylin and eosin (H&E) for cytoplasm and nucleus and indigo-carmin staining for detection of newly generated callus. Mechanical strength evaluation is performed using the "4 points bending" method.

The treatments groups are: sham osteotomy, osteotomy treated with plasma protein sponge alone, osteotomy treated with plasma protein sponge comprising glycosaminoglycan, osteotomy treated with a plasma protein sponge comprising glycosaminoglycan, optional heparin growth factors.

Another example of an animal model for bone repair is presented in Cook et al., (Am J. Vet Res 64:2-20, 2003).

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

The invention claimed is:

1. A porous, freeze-dried plasma protein matrix sponge comprising plasma proteins crosslinked by the action of thrombin, having two opposing surfaces substantially parallel to the horizontal axis of the matrix and at least one additional surface extending along the periphery of the sponge substantially parallel to the vertical axis, wherein the plasma proteins and the thrombin are present in gradients having a higher concentration along one of the opposing surfaces and, wherein the average size of the pores in cross section is smaller along the surface of the matrix exposed to the higher concentration of thrombin.

2. The porous freeze-dried plasma protein matrix sponge according to claim 1, wherein the thrombin is introduced at a concentration of about 300 IU/ml to about 1,500 IU/ml.

3. The porous freeze-dried plasma protein matrix sponge according to claim 1, wherein the thrombin is introduced at a concentration of about 500 IU/ml to about 1000 IU/mi.

4. The porous freeze-dried plasma protein matrix sponge according to claim 1, wherein the plasma proteins and thrombin are present in a ratio of about 5:1 (v/v) to about 50:1 (v/v).

5. The porous freeze-dried plasma protein matrix sponge according to claim 1, wherein the plasma proteins and thrombin are present in a ratio of about 8:1 (v/v) to about 30:1 (v/v).

6. The porous freeze-dried plasma protein matrix sponge according to claim 1, the pores having an average size of about 5 μm to about 30 μm in cross section in the fraction of the matrix exposed to the higher concentration of thrombin.

7. The porous freeze-dried plasma protein matrix sponge according to claim 1, the pores having an average size of about 10 μm to about 20 μm in cross section in the fraction of the matrix exposed to the higher concentration of thrombin.

8. The porous freeze-dried plasma protein matrix sponge according to claim 1, wherein the plasma proteins crosslinked by the action of thrombin are generated by a thrombin solution comprising at least one viscosity-enhancing agent selected from a protein, a glycosaminoglycan, a polysaccharide, disaccharide and a synthetic polymer.

9. The porous freeze-dried plasma protein matrix sponge according to claim 8, wherein the protein is an extracellular matrix protein selected from collagen, fibronectin, elastin and laminin.

10. The porous freeze-dried plasma protein matrix sponge according to claim 9, wherein the protein is collagen.

11. The porous freeze-dried plasma protein matrix sponge according to claim 9, wherein the polypeptide is fibronectin.

12. The porous freeze-dried plasma protein matrix sponge according to claim 8, wherein the glycosaminoglycan is selected from crosslinked hyaluronic acid and non-crosslinked hyaluronic acid.

13. The porous freeze-dried plasma protein matrix sponge according to claim 1, wherein the plasma proteins crosslinked by the action of thrombin are generated by a thrombin solution comprising a transglutaminase.

14. The porous freeze-dried plasma protein matrix sponge according to claim 13, wherein the transglutaminase is factor XIII.

15. The porous freeze-dried plasma protein matrix sponge according to claim 1, wherein the plasma proteins are substantially devoid of plasminogen.

16. The porous freeze-dried plasma protein matrix sponge according to claim 1, wherein the plasma proteins are substantially devoid of organic chelating agents.

17. The porous freeze-dried plasma protein matrix sponge according to claim 1, further comprising at least one additive selected from the group consisting of a polysaccharide, a glycosaminoglycan and a synthetic polymer.

18. The porous freeze-dried plasma protein matrix sponge according to claim 17, wherein the glycosaminoglycan is selected from crosslinked hyaluronic acid, non-crosslinked hyaluronic acid and heparin and derivatives thereof.

19. The porous freeze-dried plasma protein matrix sponge according to claim 1, further comprising at least one bioactive agent selected from the group consisting of growth factors, cytokines, platelets, platelet supernatant and platelet derived proteins, hormones, analgesics, anti-inflammatory agents, anti-microbials and enzymes.

20. The porous freeze-dried plasma protein matrix sponge according to claim 19, wherein the growth factor is selected from a fibroblast growth factor and variant thereof.

21. The porous freeze-dried plasma protein matrix sponge according to claim 1, further comprising cells.

22. The porous freeze-dried plasma protein matrix sponge according to claim 21, wherein the cells are selected from stem cells, progenitor cells, chondrocytes, osteoblasts, hepatocytes, mesenchymal cell types, endothelial cell types, epithelial cell types, urothelial cell types, endocrinal cell types, neuronal cell types, pancreatic cell types, renal cell types and ocular cell types.

23. The porous freeze-dried plasma protein matrix sponge according to claim 22, wherein the cells are chondrocytes.

24. The porous freeze-dried plasma protein matrix sponge according to claim 22, wherein the cells are hepatocytes.

25. The porous freeze-dried plasma protein matrix sponge according to claim 1, wherein at least one of the plasma proteins is autologous.

26. The porous freeze-dried plasma protein matrix sponge according to claim 1, wherein at least one of the plasma proteins is recombinant.

27. The porous freeze-dried plasma protein matrix sponge according to claim 1, further comprising a fibrin fiber-modifying agent.

28. A method of preparing the porous, freeze-dried plasma protein matrix sponge of claim 1, comprising the steps:
    (a) introducing a thrombin solution to a solid receptacle or mold;
    (b) layering a plasma protein solution over the thrombin solution in the solid receptacle or mold, wherein the thrombin and plasma protein solutions are introduced and layered to provide a higher concentration along one of the opposing surfaces;
    (c) incubating under conditions appropriate to achieve clotting;
    (d) freezing the clotted mixture; and
    (e) lyophilizing the clotted mixture, to obtain a porous matrix.

29. The method according to claim 28, further comprising the steps of:
    seeding the porous matrix sponge with cells.

30. The porous freeze-dried plasma protein matrix sponge according to claim 1, wherein the plasma proteins are allogeneic.

31. A method for facilitating cellular growth in an individual at a site in need of tissue repair or regeneration tissue, which comprises implanting the freeze-dried plasma protein matrix sponge of claim 1 at the site to provide a scaffold for cellular growth.

32. The method according to claim 31, wherein the site is selected from one of neural, muscular, skeletal, cartilaginous, tendonous, hepatic, pancreatic, renal, ocular, arteriovenous, mammary or urinary tissue.

33. The method according to claim 31, wherein the site is cartilage tissue.

34. The method according to claim 31, wherein the site is hepatic tissue.

35. The method according to claim 31, wherein the sponge further comprises cells.

* * * * *